United States Patent
Homma et al.

(10) Patent No.: US 11,629,280 B2
(45) Date of Patent: Apr. 18, 2023

(54) IRON POWDER FOR EXOTHERMIC COMPOSITION, PRODUCTION METHOD THEREFOR, EXOTHERMIC COMPOSITION USING SAID IRON POWDER, AND EXOTHERMIC BODY PRODUCTION METHOD

(71) Applicant: Kao Corporation, Tokyo (JP)

(72) Inventors: Taichi Homma, Utsunomiya (JP);
Ryohei Suzuki, Ichikai-machi (JP);
Takahiro Maezawa, Ichikai-machi (JP);
Tetsuya Tabata, Utsunomiya (JP)

(73) Assignee: Kao Corporation, Tokyo (JP)

( * ) Notice: Subject to any disclaimer, the term of this patent is extended or adjusted under 35 U.S.C. 154(b) by 629 days.

(21) Appl. No.: 16/612,952

(22) PCT Filed: May 18, 2018

(86) PCT No.: PCT/JP2018/019410
§ 371 (c)(1),
(2) Date: Nov. 12, 2019

(87) PCT Pub. No.: WO2018/212353
PCT Pub. Date: Nov. 22, 2018

(65) Prior Publication Data
US 2020/0157399 A1 May 21, 2020

(30) Foreign Application Priority Data

May 18, 2017 (JP) .............................. JP2017-099036
Dec. 25, 2017 (JP) .............................. JP2017-247896
Dec. 25, 2017 (JP) .............................. JP2017-247897

(51) Int. Cl.
*B22F 1/10* (2022.01)
*C06B 33/00* (2006.01)
(Continued)

(52) U.S. Cl.
CPC ................ *C09K 5/18* (2013.01); *B22F 1/105* (2022.01); *B22F 9/04* (2013.01); *B22F 9/22* (2013.01);
(Continued)

(58) Field of Classification Search
None
See application file for complete search history.

(56) References Cited

U.S. PATENT DOCUMENTS

| | | | |
|---|---|---|---|
| 3,975,186 A | 8/1976 | Grebe et al. | |
| 4,213,777 A | 7/1980 | Grebe et al. | |

(Continued)

FOREIGN PATENT DOCUMENTS

| | | |
|---|---|---|
| CN | 103889594 A | 6/2014 |
| JP | 52-24147 | 2/1977 |

(Continued)

OTHER PUBLICATIONS

English Translation of JP 04-293989 (originally published Oct. 19, 1992) from PE2E.*

(Continued)

*Primary Examiner* — George Wyszomierski
(74) *Attorney, Agent, or Firm* — Oblon, McClelland, Maier & Neustadt, L.L.P.

(57) ABSTRACT

An iron powder for an exothermic composition according to the present invention has a bulk density of 0.3 to 1.5 g/cm³. Furthermore, an exothermic composition according to the present invention contains the iron powder, a carbon material, a halide salt, and water. Furthermore, an exothermic body production method according to the present invention includes: forming a coated member by coating a base material sheet with a flowable exothermic composition containing the iron powder, a carbon material, and water; and adjusting an amount of moisture in the coated member (Continued)

by removing water from the coated member. Furthermore, the present invention is directed to a production method for the iron powder (an iron powder for an exothermic composition) including: a reducing step of reducing iron oxide to obtain reduced iron; and a step of milling the reduced iron. In the reducing step, the iron oxide is reduced by introducing iron oxide and a solid reductant with a volatile matter content of 10% by mass or more into a heating furnace whose internal portion contains no sulfur gas or is set to an air or inert gas atmosphere, and setting the internal portion to a reducing gas atmosphere through heating under a condition that an ambient temperature of the internal portion is from 900 to 1000° C.

20 Claims, 4 Drawing Sheets

(51) Int. Cl.
- *A61F 7/08* (2006.01)
- *C09K 5/18* (2006.01)
- *B22F 9/04* (2006.01)
- *B22F 9/22* (2006.01)
- *B22F 1/105* (2022.01)

(52) U.S. Cl.
CPC ............... *C06B 33/00* (2013.01); *A61F 7/08* (2013.01); *B22F 2009/045* (2013.01); *B22F 2301/35* (2013.01)

(56) References Cited

U.S. PATENT DOCUMENTS

| | | | | |
|---|---|---|---|---|
| 5,840,270 | A | * | 11/1998 | Werth ............... C01B 3/105 429/421 |
| 6,436,128 | B1 | | 8/2002 | Usui |
| 2002/0151947 | A1 | | 10/2002 | Usui |
| 2004/0081903 | A1 | | 4/2004 | Tokarski et al. |
| 2006/0147827 | A1 | | 7/2006 | Tokarski et al. |
| 2007/0209480 | A1 | | 9/2007 | Eisele et al. |
| 2012/0075770 | A1 | | 3/2012 | Banno |
| 2014/0291577 | A1 | | 10/2014 | Ugajin et al. |

FOREIGN PATENT DOCUMENTS

| | | | | |
|---|---|---|---|---|
| JP | 57-17043 | B2 | | 4/1982 |
| JP | 59-85804 | A | | 5/1984 |
| JP | 60-106874 | A | | 6/1985 |
| JP | 60-262901 | A | | 12/1985 |
| JP | 1-147003 | A | | 6/1989 |
| JP | 04/293989 | A | * | 10/1992 |
| JP | 9-75388 | A | | 3/1997 |
| JP | 11-29807 | A | | 2/1999 |
| JP | 2001-254101 | A | | 9/2001 |
| JP | 2002105501 | A | * | 4/2002 |
| JP | 2004-143180 | A | | 5/2004 |
| JP | 2004-143232 | A | | 5/2004 |
| JP | 2004-332180 | A | | 11/2004 |
| JP | 2009-34482 | A | | 2/2009 |
| JP | 2009-83856 | A | | 4/2009 |
| JP | 2009-84299 | A | | 4/2009 |
| JP | 2009-530492 | A | | 8/2009 |
| JP | 2012-72001 | A | | 4/2012 |
| JP | 2012-140537 | A | | 7/2012 |
| JP | 2012-251186 | A | | 12/2012 |
| WO | WO 2017/082183 | A1 | | 5/2017 |

OTHER PUBLICATIONS

International Search Report dated Jul. 24, 2018 in PCT/JP2018/019410 filed on May 18, 2018.

Extended European Search Report dated Jan. 18, 2021 in corresponding European Patent Application No. 18802805.4, 8 pages.

\* cited by examiner

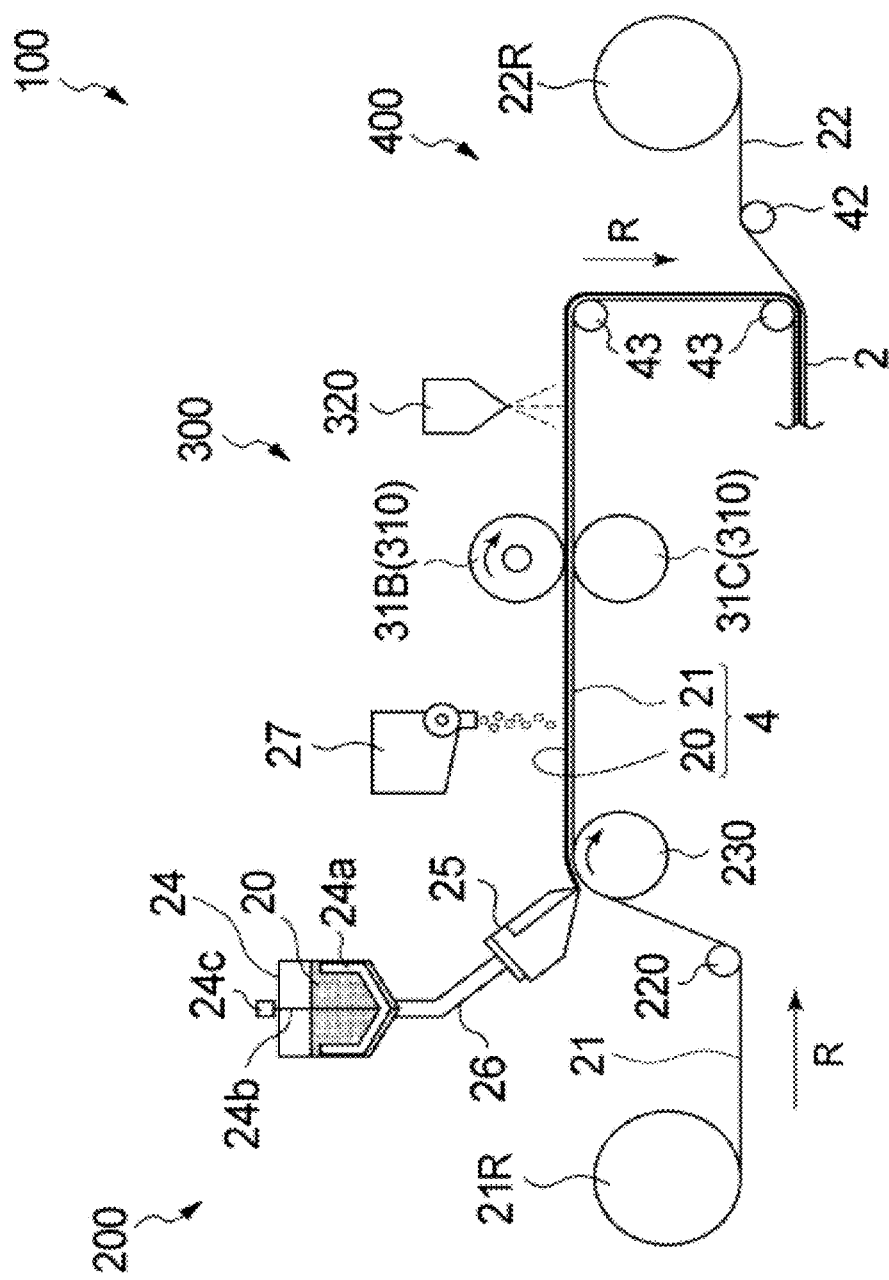

IRON POWDER FOR EXOTHERMIC COMPOSITION, PRODUCTION METHOD THEREFOR, EXOTHERMIC COMPOSITION USING SAID IRON POWDER, AND EXOTHERMIC BODY PRODUCTION METHOD

TECHNICAL FIELD

The present invention relates to an iron powder for an exothermic composition, a production method therefor, an exothermic composition using the iron powder, and an exothermic body production method.

BACKGROUND ART

Conventionally, exothermic warmers in which an exothermic body is enclosed in an air-permeable package member are widely used as disposable body warmers and the like for warming a human body. Such an exothermic body generates heat using reaction heat obtained through an oxidation reaction of an iron powder contained in the exothermic body. Since the exothermic temperature and the exothermic performance cannot be sufficiently maintained merely with an iron powder and oxygen in air, the exothermic body generally contains, in addition to the iron powder, a reaction aid such as salt or water, and activated carbon and a water-retaining agent such as an absorbent polymer carrying these substances. Patent Literature 1 states that an exothermic body is produced through a step of coating a base material in the form of a film or sheet with an exothermic composition having the above-described compositions and formed into an ink or cream form with an increased viscosity.

These sorts of products, such as disposable body warmers using an exothermic body, are required to have properties in which the temperature increase rate in an initial stage after the start of an exothermic reaction is high, the temperature immediately increases after the outer package is opened, the exothermic reaction stably continues for a long period of time after the temperature reaches a certain level of temperature, and the certain level of temperature is maintained. Exothermic properties of an exothermic body are greatly affected in particular by properties of an iron powder itself, and thus it is considered that these requests may be satisfied by using a highly active iron powder. Patent Literature 2 states that, in order to increase the oxidation reaction efficiency of an iron powder in an exothermic body, activated carbon containing an appropriate amount of water is mixed in an iron powder. Furthermore, paragraph [0020] of Patent Literature 2 states that the apparent density of an iron powder is preferably set to a range of 1.5 to 3.5 $Mg/m^3$, wherein the lower limit value of the preferable range is set to 1.5 $Mg/m^3$, because if the apparent density of an iron powder is lower than this value, the volume increases and makes it impossible to reduce the size of the body warmer.

Patent Literature 3 states that a low-density reduced iron powder with an apparent density of 0.5 to 1.5 g/cc is useful for molding applications in which compressibility and moldability are required, such as the applications for sintered parts with a complex shape that requires high moldability or the applications for sintered parts for friction material that is molded with low pressure. Furthermore, Patent Literature 3 states that the low-density reduced iron powder is produced through a step of reducing a fine powder of iron ore in a temperature range of 950 to 1150° C., thereby obtaining reduced iron, and milling the reduced iron. Note that what is mentioned in Patent Literature 3 regarding an iron powder is only those for molding applications, and there is no mention of those for exothermic composition applications.

Patent Literature 4 describes a method for producing an iron powder having a fibrous structure and preferably used to produce friction lining of brakes, couplings, and the like used in powered conveying machines, wherein, when reducing iron ore in a reducing gas atmosphere in a temperature range of 750 to 1200° C., the concentration of a gaseous sulfur compound with respect to carbon monoxide in the reducing gas atmosphere is maintained in a predetermined range, and further describes, as a method for maintaining a constant concentration of a gaseous sulfur compound in this manner, a method in which a gaseous sulfur compound is introduced from the outside and a method in which a solid sulfur compound is added to iron oxide that is to be reduced. Furthermore, Patent Literature 5 describes another method for producing an iron powder having a fibrous structure as in the iron powder described in Patent Literature 4, including a step of reducing iron oxide fine granules obtained from a pickling waste liquid through spray roasting, in a temperature range of 800 to 1000° C. in an atmosphere with carbon monoxide that does not contain sulfur dioxide to the extent possible.

CITATION LIST

Patent Literatures

Patent Literature 1: U.S. Pat. No. 6,436,128
Patent Literature 2: JP 2001-254101A
Patent Literature 3: JP S52-24147A
Patent Literature 4: U.S. Pat. No. 4,213,777
Patent Literature 5: U.S. Pat. No. 3,975,186

SUMMARY OF INVENTION

The present invention (a first aspect of the invention) is directed to an iron powder for an exothermic composition, with a bulk density of 0.3 to 1.5 $g/cm^3$.

Furthermore, the present invention (the first aspect of the invention) is directed to an exothermic composition containing an iron powder with a bulk density of 0.3 to 1.5 $g/cm^3$, a carbon material, a halide salt, and water.

Furthermore, the present invention (the first aspect of the invention) is directed to an exothermic body containing the exothermic composition according to the first aspect of the invention. Furthermore, the present invention (the first aspect of the invention) is directed to use of the iron powder for an exothermic composition according to the first aspect of the invention, for an exothermic body.

Furthermore, the present invention (a second aspect of the invention) is directed to an exothermic body production method including a step of forming a coated member by coating a base material sheet with a flowable exothermic composition containing the iron powder for an exothermic composition, with a bulk density of 0.3 to 1.5 $g/cm^3$ (the iron powder for an exothermic composition according to the first aspect of the invention), a carbon material, and water. In the second aspect of the invention, the amount of moisture in the coated member is adjusted by removing water from the coated member.

Furthermore, the present invention (a third aspect of the invention) is directed to a production method for the iron powder for an exothermic composition, with a bulk density of 0.3 to 1.5 $g/cm^3$ (the iron powder for an exothermic composition according to the first aspect of the invention). The third aspect of the invention includes a reducing step of introducing iron oxide and a solid reductant with a volatile matter content of 10% by mass or more into a heating furnace whose internal portion contains no sulfur gas or is set to an air or inert gas atmosphere, and setting the internal portion to a reducing gas atmosphere through heating under a condition that an ambient temperature of the internal portion is from 900 to 1000° C., thereby reducing the iron oxide to obtain reduced iron, and a step of milling the reduced iron.

BRIEF DESCRIPTION OF DRAWINGS

FIG. 1 is a schematic view of an embodiment of an exothermic warmer to which the present invention (the first aspect of the invention) can be applied, where FIG. 1(c) is also a schematic view of a cross-section of an exothermic body produced according to the present invention (the second aspect of the invention).

FIG. 4 is a schematic view showing another embodiment of the production apparatus shown in FIG. 3.

DESCRIPTION OF EMBODIMENTS

Figure 1A:
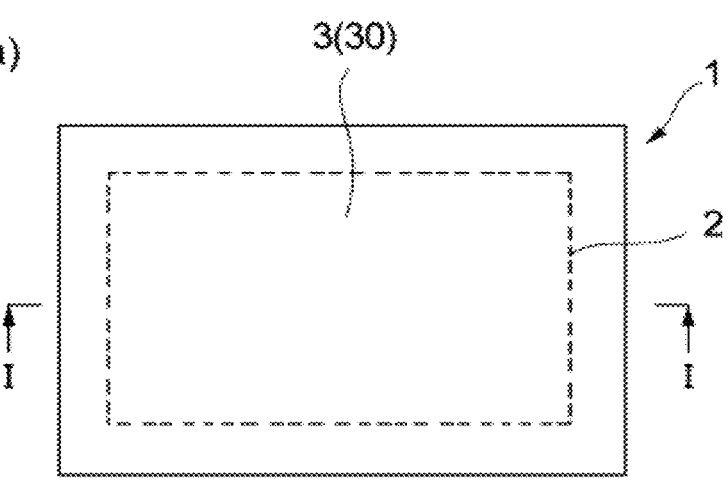
FIG. 1(a) is a plane view of the exothermic warmer.

An iron powder for an exothermic composition is required to be not only excellent in terms of exothermic properties but also excellent in terms of handleability. If an iron powder for an exothermic composition is excellent in terms of handleability, when a flowable coating material capable of being used for coating is formed by adding activated carbon, water, and the like to the iron powder, the coating material is excellent in terms of preservation stability, and is unlikely to have issues such as sedimentation of the iron powder for an exothermic composition, and an increase in the viscosity or gelling of the coating material, and thus it is possible to efficiently produce an exothermic body. However, an iron powder for an exothermic composition, and an exothermic composition that are excellent in terms of both exothermic properties and handleability have not been provided.

Accordingly, the first aspect of the invention relates to an iron powder for an exothermic composition, and an exothermic composition that are excellent in terms of exothermic properties and handleability.

Furthermore, the third aspect of the invention relates to a production method for the iron powder for an exothermic composition, with which it is possible to efficiently produce an iron powder for an exothermic composition, which is excellent in terms of exothermic properties and handleability.

Furthermore, in the case of using a raw material such as an iron powder for an exothermic composition, with a low bulk density (the iron powder for an exothermic composition according to the first aspect of the invention) in production of an exothermic body, moisture is likely to be retained in voids in raw material particles and between raw material particles, and thus it is necessary to form a flowable exothermic composition, by increasing the amount of moisture that is to be added, to an amount larger than usual.

If the amount of moisture that is to be added to the exothermic composition is increased in order to improve the flowability of the exothermic composition, the ability of the exothermic composition to coat the base material is improved. However, an oxidation reaction (exothermic reaction) due to contact between the iron powder for an exothermic composition and air is suppressed by an excessive amount of moisture, and the amount of heat necessary to increase the temperature increases in accordance with an increase in the heat capacity of the exothermic body, and thus the exothermic properties of the exothermic body deteriorate.

Accordingly, the second aspect of the invention relates to providing a production method for an exothermic body that contains an iron powder for an exothermic composition, with a low bulk density, and is excellent in terms of exothermic properties.

The iron powder for an exothermic composition according to the first aspect of the invention is used as a material for an exothermic composition. The exothermic composition generates heat using heat obtained through an oxidation reaction between an iron powder (oxidizable metal) and oxygen in air, and is used typically as an exothermic body in exothermic warmers such as disposable body warmers. The exothermic warmer to which the first aspect of the invention can be applied is preferably used to warm a human body by being directly attached to the human body, or being attached to clothes. Examples of the contact region in a human body include shoulders, a neck, a face, eyes, a waist, elbows, knees, thighs, lower legs, an abdomen, a lower abdomen, hands, soles, and the like. Furthermore, the exothermic warmer to which the first aspect of the invention can be applied is preferably used to warm various articles other than a human body, or to keep them warm, for example, by being attached thereto.

Hereinafter, the exothermic composition and the iron powder according to the first aspect of the invention will be described based on preferred embodiments with reference to the drawings.

FIG. 1 shows an exothermic warmer 1, which is an embodiment of an exothermic warmer to which the first aspect of the invention can be applied. As shown in FIG. 1(a), the exothermic warmer 1 includes an exothermic body 2 and a package member 3 that wraps around the exothermic body 2. The exothermic body 2 is a member that generates heat in the exothermic warmer 1, and contains an exothermic composition 20 containing the iron powder for an exothermic composition according to the first aspect of the invention. The package member 3 is a member that wraps around the entire exothermic body 2 and forms the outer face of the exothermic warmer 1, and part of or the entire package member 3 is air-permeable. In the exothermic warmer 1, the exothermic body 2 is not fixed to the package member 3, and thus can be moved independently of the package member 3.

Figure 1B:
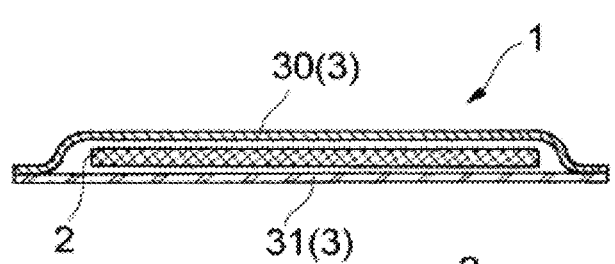
FIG. 1(b) is a cross-sectional view taken along the line I-I in FIG. 1(a)

As shown in FIG. 1(b), the package member 3 includes a first cover sheet 30 and a second cover sheet 31. The first cover sheet 30 and the second cover sheet 31 respectively have extending regions extending outward from the peripheral edge of the exothermic body 2, and the extending regions are joined to each other. This joining is preferably airtight joining continuously arranged in the shape of a ring that surrounds the exothermic body 2. The internal portion of the package member 3 formed by joining the cover sheets 30 and 31 to each other has a space for accommodating the exothermic body 2, and the exothermic body 2 is accommodated in this space.

Figure 1C:
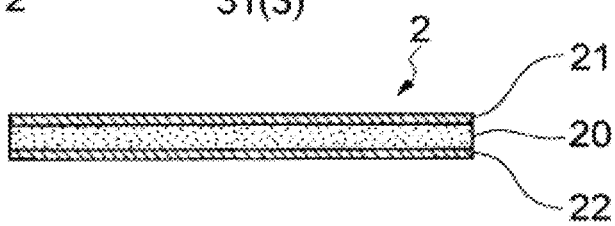
FIG. 1(c) is a schematic view showing an enlarged cross-section of an exothermic body in the exothermic warmer shown in FIG. 1(b). The exothermic warmer of FIG. 1 is an embodiment of an exothermic warmer using an iron powder for an exothermic composition produced through the production method according to the present invention (the third aspect of the invention). Furthermore.

As shown in FIG. 1(c), the exothermic body 2 has a configuration in which the exothermic composition 20 is interposed between two base material sheets 21 and 22. As the base material sheets 21 and 22, it is possible to use sheets conventionally used in conventional techniques, and examples thereof include air-impermeable materials such as synthetic resin films, air-permeable materials made of fibrous sheets such as nonwoven fabrics or paper, laminates of the air-impermeable materials and the fibrous sheets, and the like. Furthermore, the base material sheets 21 and 22 may have high water-absorbing properties, and, in this case, examples thereof include fibrous sheets containing hydrophilic fibers, fibrous sheets containing absorbent polymer particles and hydrophilic fibers, and the like. The base material sheets 21 and 22 may be the same or may be different from each other.

The exothermic composition 20 contains an iron powder (the iron powder for an exothermic composition according to the first aspect of the invention), which is a type of oxidizable metal, a carbon material, a halide salt, and water. In this manner, the exothermic composition 20 in the exothermic body 2 is a water-containing layer that contains water, and the halide salt contained in the exothermic composition 20, that is, an electrolyte is dissolved in water in the exothermic composition 20. The exothermic composition 20 generates heat using heat obtained through an oxidation reaction between the iron powder and oxygen in air.

The iron powder for an exothermic composition according to the first aspect of the invention contained in the exothermic composition 20 is characterized by having a bulk density in a range of 0.3 to 1.5 $g/cm^3$. The bulk density of an iron powder for an exothermic composition commonly used in conventional examples is typically more than 1.5 $g/cm^3$ and is in a range of 1.8 to 2.5 $g/cm^3$, and thus the iron powder for an exothermic composition according to the first aspect of the invention can be said to have a lower bulk density and a larger volume than those of conventional products.

The bulk density of the iron powder (the iron powder for an exothermic composition) in the first aspect of the invention is measured using a bulk density measuring device (JIS bulk specific gravity measuring device JISZ-2504, manufactured by Tsutsui Rikagaku Kikai Co., Ltd.) according to JIS Z-2504 Metallic powders—Determination of apparent density.

The iron powder for an exothermic composition according to the first aspect of the invention has a bulk density in a specific range of 0.3 to 1.5 $g/cm^3$, and thus the exothermic properties of an exothermic composition containing the iron powder can be significantly improved. Specifically, in a comparison with a conventional iron powder for an exothermic composition, with a bulk density of more than 1.5 $g/cm^3$, the reaction ratio in the oxidation reaction of the iron powder for an exothermic composition according to the first aspect of the invention can be greatly improved, and the amount of heat generated by the exothermic composition can be increased. That is to say, with the iron powder for an exothermic composition according to the present invention, for example, an exothermic reaction at a temperature similar to that of conventional products can be continued for a longer period of time than the conventional products at an iron powder amount similar to that of conventional products, and, furthermore, for example, an exothermic reaction at a temperature similar to that of conventional products can be continued at an iron powder amount smaller than that of the conventional products. The iron powder for an exothermic composition according to the first aspect of the invention has a high reaction ratio in the oxidation reaction of the iron powder and a large amount of heat generated by the exothermic composition in this manner, and thus, for example, this iron powder is useful to reduce the thickness of an exothermic composition or an exothermic body using the exothermic composition, and, furthermore, for example, the heat generation time can be controlled with relative ease, and thus the degree of freedom in designing an exothermic body can be improved. If the bulk density of an iron powder for an exothermic composition is more than 1.5 $g/cm^3$, it is difficult to obtain such excellent exothermic properties. Furthermore, if the bulk density of an iron powder for an exothermic composition is less than 0.3 $g/cm^3$, it may be difficult to handle the iron powder, and it is difficult to reduce the thickness of the exothermic composition in an exothermic body and the like. The bulk density of the iron powder for an exothermic composition according to the first aspect of the invention is preferably 0.4 $g/cm^3$ or more, and more preferably 0.5 $g/cm^3$ or more, and is preferably 1.4 $g/cm^3$ or less, and more preferably 1.3 $g/cm^3$ or less. The exothermic properties of an exothermic composition or an exothermic body can be evaluated using an exothermic profile obtained by plotting the temperature and the time when causing an exothermic reaction of the exothermic composition to occur, and can be evaluated using an area obtained by integrating the temperature with the time, for example, as described later.

As a method for improving these sorts of exothermic properties of an exothermic body, there is a conventionally known method in which an iron powder with a relatively small particle size is used as an iron powder for an exothermic composition. However, generally, when the particle size of an iron powder for an exothermic composition is small, the preservation stability of a coating material (slurry-like exothermic composition) prepared by adding a carbon material, a halide salt, water, and the like to the iron powder decreases, and issues such as sedimentation of the iron powder, and an increase in the viscosity or gelling of the coating material are likely to occur, and thus the handleability of the coating material decreases such as sending the coating material as a slurry and coating with the coating material being difficult. Such a coating material with low handleability is difficult to use in industrial production of exothermic bodies.

In regards to this aspect, the iron powder for an exothermic composition according to the first aspect of the invention does not have a particle size, but rather has a bulk density within the above-described specific range, and thus the exothermic properties can be improved without decreasing the handleability of the exothermic composition. Specifically, if a coating material (slurry-like exothermic composition) is formed by adding a carbon material, a halide salt, and water to the iron powder for an exothermic composition according to the first aspect of the invention, the coating material is excellent in terms of preservation stability, and is unlikely to have issues such as sedimentation of the iron powder, and an increase in the viscosity or gelling of the coating material, and thus the exothermic body can be efficiently used in industrial production.

As described in Patent Literature 3, an iron powder with a bulk density in a range of 1.5 g/cm³ or less is known. However, what is mentioned in Patent Literature 3 is that an iron powder with a low bulk density is used for molding applications, and there is no mention of exothermic compositions in Patent Literature 3, and naturally there is neither mention nor suggestion of the fact that the exothermic properties and the handleability of an exothermic composition are improved through application of the technical idea of the first aspect of the invention, that is, by using an iron powder with a low bulk density for an exothermic composition. Meanwhile, in the technical field of exothermic bodies such as disposable body warmers, a conventional main issue is to reduce the size of exothermic bodies. As described in paragraph [0020] of Patent Literature 2, it is common technical knowledge that, if the bulk density of an iron powder for an exothermic composition is less than 1.5 g/cm³, the volume of an exothermic body increases, which makes it difficult to reduce the size of the exothermic body. That is to say, in a current state, an iron powder for an exothermic composition, with a bulk density in a range of 1.5 g/cm³ or less, such as the iron powder for an exothermic composition according to the first aspect of the invention, has not been substantially used for exothermic body applications.

The average particle size of the preferable iron powder for an exothermic composition according to the first aspect of the invention is preferably 30 μm or more, and more preferably 40 μm or more, and is preferably 150 μm or less, and more preferably 100 μm or less. If the average particle size of the iron powder for an exothermic composition is within this range, the above-described effects (the effects of improving the exothermic properties and the handleability of an exothermic composition or an exothermic body) can be more reliably achieved. As the average particle size of the iron powder, for example, a volume-based median diameter as measured using a laser diffraction particle size distribution analyzer is used. Specifically, for example, a method is used in which a measurement is performed using an LA-950V2 manufactured by Horiba, Ltd. with a standard wet circulation cell with settings in which the refractive index of the iron powder is 3.5 for the real part and 3.8i for the imaginary part, water is used as a dispersion medium and the refractive index thereof is 1.33, the circulation speed is 15, and the agitation is 5, and the thus obtained volume-based median diameter is taken as a measurement result of the average particle size of the iron powder.

Furthermore, the BET specific surface area of the preferable iron powder for an exothermic composition according to the first aspect of the invention is preferably 0.1 m²/g or more, and more preferably 0.2 m²/g or more. If the BET specific surface area of the iron powder for an exothermic composition is within this range, the above-described effects (the effects of improving the exothermic properties and the handleability of an exothermic composition or an exothermic body) can be more reliably achieved. There is no particular limitation on the upper limit value of the BET specific surface area of the preferable iron powder for an exothermic composition according to the first aspect of the invention, but, in order to increase the activity of the oxidation reaction when using the iron powder and also to prevent the exothermic performance from decreasing due to oxidization of the iron powder during preservation before use, the BET specific surface area is preferably 50 m²/g or less, and more preferably 40 m²/g or less. The BET specific surface area of the iron powder is measured using a known BET method. The BET method is a method in which the specific surface area of a powder is measured by measuring the amount of nitrogen, argon, or the like adsorbed to the powder surface.

Furthermore, the pore volume of the preferable iron powder for an exothermic composition according to the first aspect of the invention as measured using the mercury intrusion method, in a range of 1 μm or more, is preferably 0.3 cm³/g or more, and more preferably 0.5 cm³/g or more. When the pore volume of the preferable iron powder for an exothermic composition according to the first aspect of the invention as measured using the mercury intrusion method, in a range of 1 μm or more, is within the above-described specific range, the total pore volume thereof is preferably 0.3 cm³/g or more, and more preferably 0.5 cm³/g or more. If the pore volume of the iron powder for an exothermic composition as measured using the mercury intrusion method is within this range, the above-described effects (the effects of improving the exothermic properties and the handleability of an exothermic composition or an exothermic body) can be more reliably achieved. There is no particular limitation on the upper limit value of the pore volume of the preferable iron powder for an exothermic composition according to the first aspect of the invention as measured using the mercury intrusion method, but, in order to prevent the bulk density from decreasing due to a too large pore volume of the iron powder, to allow the iron powder to be handled with ease, and to easily reduce the thickness of an exothermic composition in an exothermic body and the like, the pore volume, in a range of 1 μm or more, is preferably 4.0 cm³/g or less, and more preferably 3.0 cm³/g or less, and the total pore volume is preferably 4.0 cm³/g or less, and more preferably 3.0 cm³/g or less. The pore volume of the iron powder as measured using the mercury intrusion method is measured, for example, using a method as defined by JIS R1655.

The preferable iron powder for an exothermic composition according to the first aspect of the invention is produced through a step of milling reduced iron that is a raw material, and the average particle size, the BET specific surface area, and the pore volume as measured using the mercury intrusion method can be adjusted by adjusting the milling level in the milling step as appropriate.

In the preferable iron powder for an exothermic composition according to the first aspect of the invention, the metal iron content is preferably 60% by mass or more, and more preferably 70% by mass or more, and is preferably 95% by mass or less, and more preferably 90% by mass or less. If the metal iron content in the iron powder for an exothermic composition is within this range, the above-described effects (the effects of improving the exothermic properties and the handleability of an exothermic composition or an exothermic body) can be more reliably achieved. The metal iron content in the iron powder is measured, for example, using the bromine-methanol titrimetric method as defined by ISO5416. The metal iron content in the iron powder can be adjusted by adjusting the reducing conditions, the heating conditions after reduction, and the like as appropriate.

Note that the preferable iron powder for an exothermic composition according to the first aspect of the invention may contain, as components other than the metal iron, for example, approximately 3% by mass or less of silica ($SiO_2$), approximately 15% by mass or less of carbon (C), and approximately 3% by mass or less of alumina ($Al_2O_3$).

Usually, this sort of iron powder partially inevitably oxidizes by reacting with oxygen in air at room temperature, and thus the preferable iron powder for an exothermic composition according to the first aspect of the invention may contain approximately 10% by mass or less of oxygen (O). These components other than the metal iron are inevitably mixed mainly in a step of producing an iron powder for an exothermic composition, and are not especially important in achieving the above-described predetermined effects of the first aspect of the invention.

Figure 2A:
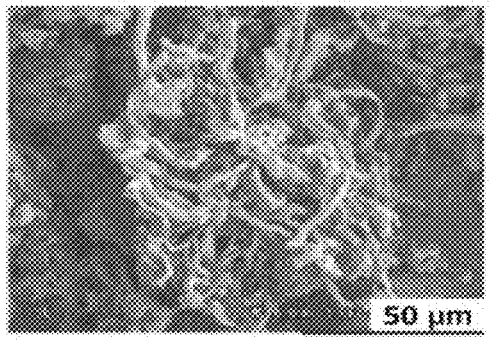
FIG. 2(a) is an electron micrograph (1000 times) of an example of an iron powder for an exothermic composition according to the present invention (the first aspect of the invention)
Figure 2B:
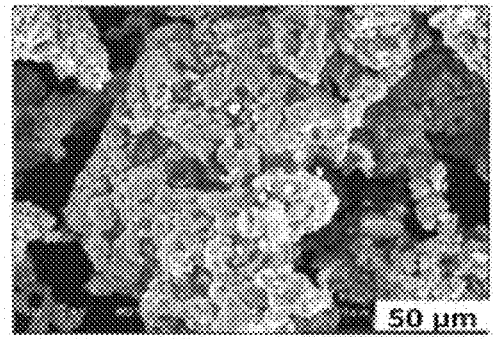
FIG. 2(b) is an electron micrograph (1000 times) of an example of a conventional iron powder for an exothermic composition. The electron micrograph in FIG. 2(a) is also an electron micrograph (1000 times) of an example of an iron powder for an exothermic composition produced through the production method according to the present invention (the third aspect of the invention).

The preferable iron powder for an exothermic composition according to the first aspect of the invention is characterized not only the various physical properties described above but also the external appearance. FIG. 2(a) is an electron micrograph of an example of the preferable iron powder for an exothermic composition according to the first aspect of the invention, and FIG. 2(b) is an electron micrograph of a conventional iron powder for an exothermic composition (iron powder with a bulk density of more than 1.5 g/cm$^3$). As shown in FIG. 2(a), the preferable iron powder for an exothermic composition according to the first aspect of the invention is characterized in that the surface layer is constituted by a large number of fibrous matters that are arranged at random in three dimensions. In the surface layer of the conventional iron powder for an exothermic composition shown in FIG. 2(b), an aggregate of such fibrous matters can hardly be seen. It is not clear how such characteristics (having a fibrous structure) of the external appearance of the preferable iron powder for an exothermic composition according to the first aspect of the invention affect the development of the above-described actions and effects of the iron powder, but it is clear also from an observation using an electron microscope in this manner that the preferable iron powder for an exothermic composition according to the first aspect of the invention is clearly different from a conventional iron powder for an exothermic composition. The fiber diameter of the fibrous matters constituting the preferable iron powder for an exothermic composition according to the first aspect of the invention is approximately 10 μm or less. The fiber diameter of the fibrous matters is measured, for example, by performing image analysis on an electron micrograph and measuring a distance between two points.

The preferable iron powder for an exothermic composition according to the first aspect of the invention is obtained by performing reduction treatment on iron ore containing iron oxide (III) that is a raw material, using a solid reductant in a reducing furnace such as a rotary kiln, thereby obtaining reduced iron, milling the reduced iron using a mill, and, as necessary, sieving the resultant substance into particles with a desired particle size. This series of processes is basically the same as those in a conventional method for producing an iron powder for an exothermic composition. When obtaining the preferable iron powder for an exothermic composition according to the first aspect of the invention, a milling condition of reduced iron is particularly important. That is to say, in order to obtain the preferable iron powder for an exothermic composition according to the first aspect of the invention, it is preferable that the milling level of the reduced iron is lower than that in conventional production of an iron powder for an exothermic composition. For example, in production of a conventional iron powder for an exothermic composition, generally, milling is performed on 1.0 kg of reduced iron for approximately 8 to 12 minutes using a vibration rod mill (e.g., product name "MB-1" manufactured by Chuo Kakohki Co., Ltd.), whereas, in production of the preferable iron powder for an exothermic composition according to the first aspect of the invention, milling is performed on 0.1 kg of reduced iron for approximately 5 to 30 seconds at a number of rotations of 700 to 1000 rpm using a vibratory disc mill (e.g., product name "RS200" manufactured by Verder Scientific Co., Ltd.). When such a relatively low level of milling is performed on reduced iron, it is possible to obtain an iron powder with a bulk density in a range of 0.3 to 1.5 g/cm$^3$.

Hereinafter, the exothermic warmer 1 shown in FIG. 1 will be further described. From the viewpoint of maintaining a stable exothermic reaction for a long period of time, the content of the iron powder (the preferable iron powder for an exothermic composition according to the first aspect of the invention) in the exothermic composition 20 is preferably 20% by mass or more, and more preferably 30% by mass or more, and is preferably 70% by mass or less, and more preferably 60% by mass or less, with respect to the total mass of the exothermic composition 20. From similar viewpoints, the basis weight of the iron powder (the preferable iron powder for an exothermic composition according to the first aspect of the invention) in the exothermic composition 20 is preferably 80 g/m$^2$ or more, and more preferably 120 g/m$^2$ or more, and is preferably 1400 g/m$^2$ or less, and more preferably 1200 g/m$^2$ or less.

The exothermic composition 20 further contains a carbon material, in addition to the preferable iron powder for an exothermic composition according to the first aspect of the invention described above. Examples of the carbon material include those that function as a moisture retaining agent, and an oxygen retaining/supplying agent to an iron powder, and examples thereof include activated carbon (coconut shell carbon, charcoal powder, bituminous coal, peat, and lignite), carbon black, acetylene black, black lead, graphite, coal, coal char, and the like, which may be used alone or in combination of two or more. Of these carbon materials, activated carbon is particularly preferable because it has a high specific surface area. The carbon material content in the exothermic composition 20 is preferably 3 parts by mass or more, and more preferably 5 parts by mass or more, and is preferably 30 parts by mass or less, and more preferably 25 parts by mass or less, with respect to 100 parts by mass of the iron powder in the exothermic composition 20.

The exothermic composition 20 further contains a halide salt. Examples of the halide salt include those that can function as an electrolyte in which oxide formed on the iron powder surface can be dissolved, and examples thereof include sodium chloride, potassium chloride, calcium chloride, magnesium chloride, ferrous chloride, ferric chloride, and the like, which may be used alone or in combination of two or more. Of these halide salts, sodium chloride is particularly preferable because it is excellent in terms of conductivity, chemical stability, production cost, and the like. The content of the halide salt in the exothermic composition 20 is preferably 3 parts by mass or more, and more preferably 5 parts by mass or more, and is preferably 30 parts by mass or less, and more preferably 25 parts by mass or less, with respect to 100 parts by mass of the iron powder in the exothermic composition 20.

The exothermic composition 20 further contains water. As described above, the exothermic composition 20 contains water, and the halide salt is dissolved in this water. The exothermic composition containing water is a flowable slurry composition. From the viewpoint of reactivity, the water content in the exothermic composition is preferably 30% by mass or more, and more preferably 40% by mass or more, and is preferably 70% by mass or less, and more preferably 60% by mass or less, with respect to the total mass of the exothermic composition 20.

The exothermic composition 20 may contain, in addition to the above-described components (the iron powder, the carbon material, the halide salt, and the water), zeolite, pearlite, vermiculite, silica, alumina, titania, and the like as necessary as a reaction accelerator having a similar function to that of the carbon material. Furthermore, from the viewpoint of improving the suitability as a coating material, the exothermic composition 20 may contain various thickeners and surfactants. Examples of the thickeners include substances that mainly absorb water or an aqueous solution of metal chloride, thereby increasing the consistency or providing the thixotropy, and examples thereof include bentonite, stearate, polyacrylate such as sodium polyacrylate; gelatin, tragacanth gum, locust bean gum, guar gum, gum arabic, alginate such as sodium alginate; pectin, carboxyvinyl polymer, dextrin, starch-based absorbent such as pregelatinized starch and starch for processing; polysaccharide-based thickeners such as carrageenan and agar; cellulose derivative-based thickeners such as carboxymethylcellulose, ethylcellulose acetate, hydroxyethylcellulose, methylcellulose, and hydroxypropylcellulose, and the like. Examples of the surfactants include anionic surfactants containing, as a main component, a condensate of aromatic sulfonic acid and formalin or a special carboxylic acid-type high-molecular surfactant.

Typically, the exothermic body 2 is produced by preparing a coating material by mixing components (an iron powder, a carbon material, water, etc.) other than a halide salt (coating material preparing step), coating a base material sheet 21 with this coating material (coating step), adding a halide salt to the coating material after coating (electrolyte adding step), and overlaying another base material sheet 22 on the coating material (sheet overlaying step). In the electrolyte adding step, an exothermic composition 20 in the form of a slurry is obtained by adding a halide salt to the coating material on the base material sheet 21.

In the coating material preparing step, a halide salt, that is, an electrolyte is not added to the coating material, in order to improve the dispersibility of the coating material component, and to reduce the loss of generated heat by preventing oxidization of the iron powder during preservation of the coating material.

In the electrolyte adding step, a halide salt, that is, an electrolyte is added in a solid state. If a halide salt is added in a solid state, advantageous effects can be achieved in which corrosion of the device is suppressed compared with a case in which it is added in the form of an aqueous solution, and dispersion of the halide salt to the device and/or its surroundings is suppressed.

In the coating step, a fibrous sheet not containing an absorbent polymer but containing a hydrophilic fiber (e.g., nonwoven fabrics or paper) is preferably used as the base material sheet 21 that is coated with the coating material. In the sheet overlaying step, a fibrous sheet (super absorbent sheet) containing an absorbent polymer is preferably used as the base material sheet 22 that is overlaid on the coating material after coating. If a super absorbent sheet is overlaid on the coating material after coating in this manner, the amount of moisture in the exothermic composition 20 can be easily adjusted such that an exothermic reaction is allowed to occur. The absorbent polymer content in the super absorbent sheet is usually approximately 10 to 70% by mass with respect to the total mass of the super absorbent sheet.

The basis weight of the exothermic body 2 is adjusted as appropriate according to the applications and the like of the exothermic warmer 1, and it is preferably 100 $g/m^2$ or more, and more preferably 150 $g/m^2$ or more, and is preferably 2500 $g/m^2$ or less, and more preferably 2000 $g/m^2$ or less.

The basis weight of the exothermic composition 20 is preferably 50 $g/m^2$ or more, and more preferably 100 $g/m^2$ or more, and is preferably 1200 $g/m^2$ or less, and more preferably 1000 $g/m^2$ or less.

The basis weight of the base material sheets 21 and 22 is preferably 10 $g/m^2$ or more, and more preferably 20 $g/m^2$ or more, and is preferably 200 $g/m^2$ or less, and more preferably 150 $g/m^2$ or less.

In the exothermic warmer 1 shown in FIG. 1, the exothermic body 2 is enclosed in the package member 3 constituted by the first cover sheet 30 and the second cover sheet 31. Part or the entirety of either the first cover sheet 30 or the second cover sheet 31 is air-permeable. It is also possible that both the first cover sheet 30 and the second cover sheet 31 are air-permeable. If the package member 3 is air-permeable, oxygen is smoothly supplied to the exothermic composition 20 in the exothermic body 2, and a stable exothermic reaction is maintained for a long period of time. As the air-permeable sheet that can be used as the package member 3 (the cover sheets 30 and 31), for example, it is preferable to use a porous sheet made of a synthetic resin that is moisture-permeable but is not water-permeable. When using this porous sheet, it is possible to improve the texture of the package member 3 by laminating various fibrous sheets such as nonwoven fabrics (e.g., needle-punched nonwoven fabrics or air-through nonwoven fabrics) on the outer face (face oriented outward) of the porous sheet.

If one of the cover sheets (e.g., the first cover sheet 30) is air-permeable, the other cover sheet (e.g., the second cover sheet 31) may be a sheet that is less air-permeable than the first cover sheet 30, and, in this case, vapor can be more stably generated via the first cover sheet 30. The phrase "less air-permeable sheet" includes both a case in which the sheet is partially air-permeable but its air-permeability level is lower than that of the first cover sheet 30, and a case in which the sheet is an air-impermeable sheet that is not air-permeable. If the second cover sheet 31 is an air-impermeable sheet, the air-impermeable sheet may be a film made of a synthetic resin, or a composite sheet obtained by laminating various fibrous sheets such as nonwoven fabrics (e.g., needle-punched nonwoven fabrics or air-through nonwoven fabrics) on the outer face (face oriented outward) of the film.

It is also possible that an outer face of the package member 3 has an adhesive layer (not shown) that is formed through coating with an adhesive. The adhesive layer is used to attach the exothermic warmer according to the first aspect of the invention, to the human skin, clothes, or the like. Examples of the adhesive constituting the adhesive layer include those that have been conventionally used in the art, such as a hot-melt adhesive. In order not to deteriorate air-permeability, it is preferable that an adhesive layer is provided at the peripheral edge of the package member 3.

The first aspect of the invention was described above based on an embodiment thereof, but the first aspect of the invention is not limited to the foregoing embodiment, and may be changed as appropriate.

There is no particular limitation on the form of the exothermic warmer to which the first aspect of the invention can be applied, and the first aspect of the invention can be applied not only to a commonly used exothermic warmer including an exothermic body and a package member that wraps around the exothermic body, but also to, for example, an exothermic warmer not containing a package member and constituted only by an exothermic body. Furthermore, the exothermic body may be an integrated product in which an exothermic composition containing an iron powder is integrated to form a predetermined shape (e.g., a sheet form), or may be a fluid in which an exothermic composition is not integrated.

Regarding the foregoing embodiment of the first aspect of the invention, the following notes are further disclosed.

<A1>
An iron powder for an exothermic composition, with a bulk density of 0.3 to 1.5 g/cm$^3$.

<A2>
An exothermic composition containing the iron powder for an exothermic composition (the iron powder with a bulk density of 0.3 to 1.5 g/cm$^3$) as set forth in clause <A1>, a carbon material, a halide salt, and water.

<A3>
The exothermic composition as set forth in clause <A2>, wherein the bulk density is preferably 0.4 g/cm$^3$ or more, and more preferably 0.5 g/cm$^3$ or more, and is preferably 1.4 g/cm$^3$ or less, and more preferably 1.3 g/cm$^3$ or less.

<A4>
The exothermic composition as set forth in clause <A2> or <A3>, wherein an average particle size of the iron powder is from 20 to 150 μm.

<A5>
The exothermic composition as set forth in any one of clauses <A2> to <A4>, wherein an average particle size of the iron powder is preferably 30 μm or more, and more preferably 40 μm or more, and is preferably 150 μm or less, and more preferably 100 μm or less.

<A6>
The exothermic composition as set forth in any one of clauses <A2> to <A5>, wherein a metal iron content of the iron powder is from 60 to 95% by mass.

<A7>
The exothermic composition as set forth in any one of clauses <A2> to <A6>, wherein a metal iron content of the iron powder is preferably 60% by mass or more, and more preferably 70% by mass or more, and is preferably 95% by mass or less, and more preferably 90% by mass or less.

<A8>
The exothermic composition as set forth in any one of clauses <A2> to <A7>, wherein a BET specific surface area of the iron powder is 0.1 m$^2$/g or more.

<A9>
The exothermic composition as set forth in any one of clauses <A2> to <A7>, wherein a BET specific surface area of the iron powder is preferably 0.1 m$^2$/g or more, and more preferably 0.2 m$^2$/g or more, and is preferably 50 m$^2$/g or less, and more preferably 40 m$^2$/g or less.

<A10>
The exothermic composition as set forth in any one of clauses <A2> to <A9>, wherein the exothermic composition is a flowable slurry composition.

<A11>
The exothermic composition as set forth in any one of clauses <A2> to <A10>, wherein a water content is preferably 30% by mass or more, and more preferably 40% by mass or more, and is preferably 70% by mass or less, and more preferably 60% by mass or less.

<A12>
The exothermic composition as set forth in any one of clauses <A2> to <A11>, wherein a pore volume of the iron powder as measured using a mercury intrusion method, in a range of 1 μm or more, is 0.3 cm$^3$/g or more.

<A13>
The exothermic composition as set forth in any one of clauses <A2> to <A12>, wherein a pore volume of the iron powder as measured using a mercury intrusion method, in a range of 1 μm or more, is preferably 0.3 cm$^3$/g or more, and more preferably 0.5 cm$^3$/g or more, and is preferably 4.0 cm$^3$/g or less, and more preferably 3.0 cm$^3$/g or less.

<A14>
The exothermic composition as set forth in any one of clauses <A2> to <A13>, wherein a surface layer of the iron powder is constituted by a large number of fibrous matters that are arranged at random in three dimensions.

<A15>
The exothermic composition as set forth in any one of clauses <A2> to <A14>, wherein a basis weight is preferably 50 g/m$^2$ or more, and more preferably 100 g/m$^2$ or more, and is preferably 1200 g/m$^2$ or less, and more preferably 1000 g/m$^2$ or less.

<A16>
The exothermic composition as set forth in any one of clauses <A2> to <A15>, wherein a content of the iron powder is preferably 20% by mass or more, and more preferably 30% by mass or more, and is preferably 70% by mass or less, and more preferably 60% by mass or less.

<A17>
The exothermic composition as set forth in any one of clauses <A2> to <A16>, wherein a basis weight of the iron powder is preferably 80 g/m$^2$ or more, and more preferably 120 g/m$^2$ or more, and is preferably 1400 g/m$^2$ or less, and more preferably 1200 g/m$^2$ or less.

<A18>
An exothermic body containing the exothermic composition as set forth in any one of clauses <A2> to <A17>.

<A19>
The exothermic body as set forth in clause <A18>, wherein a basis weight is preferably 100 g/m$^2$ or more, and more preferably 150 g/m$^2$ or more, and is preferably 2500 g/m$^2$ or less, and more preferably 2000 g/m$^2$ or less.

<A20>
The exothermic body as set forth in clause <A18> or <A19>, wherein the exothermic body has a configuration in which the exothermic composition is interposed between two base material sheets, and a basis weight of the base material sheets is preferably 10 g/m$^2$ or more, and more preferably 20 g/m$^2$ or more, and is preferably 200 g/m$^2$ or less, and more preferably 150 g/m$^2$ or less.

<A21>
Use of the iron powder as set forth in clause <A1>, for an exothermic body.

EXAMPLES

Hereinafter, the first aspect of the invention will be more specifically described by way of examples, but the first aspect of the invention is not limited to these examples.

Example A1

Iron oxide (III) (32225-0401 manufactured by Junsei Chemical Co., Ltd.) was used as an iron source, and a coconut shell carbon (LP16-042 manufactured by Osaka Gas Chemicals Co., Ltd.) was used as a solid reductant. A mixed powder was obtained by placing 6 g of iron source and 2 g of solid reductant in a polyethylene bag (Unipack F-8 manufactured by Seisannipponsha Ltd.) and shaking the bag, and the mixed powder was filled into a tube made of SUS303 with an inner diameter of 20 mm and a length of 50 mm to a filling height of 35 mm. The iron source in a filled state was subjected to reduction treatment using an atmosphere furnace (KDF-900GL manufactured by Denken. Co. Ltd.) to obtain a reduced iron block. The reduction treatment was performed in a nitrogen atmosphere by increasing the temperature from room temperature at 15° C./min to 950° C., keeping the temperature at 950° C. for 1 hour, and then slowly cooling the resultant substance to room temperature. The reduced iron block was taken out from the tube, and milled at a number of rotations of 700 rpm for 10 seconds using a vibratory disc mill (RS200 (standard mill set made of SUS) manufactured by Verder Scientific Co., Ltd.) to obtain a coarse iron powder. A coarse powder was removed from the obtained coarse iron powder through sieving for 5 minutes using a rotating and tapping test apparatus (1038-A manufactured by Yoshida Manufacturing Co., Ltd.) with a test sieve (JTS-250-60-37 manufactured by Tokyo Screen Co., Ltd.) with a sieve opening size of 250 µm, to obtain a target iron powder for an exothermic composition.

Example A2

An iron powder for an exothermic composition was obtained as in Example A1, except that 16 g of iron source and 4 g of solid reductant were used, and a tube made of SUS303 with an inner diameter of 48 mm and a length of 150 mm was used.

Example A3

An iron powder for an exothermic composition was obtained as in Example A2, except that the reduction treatment was performed by increasing the temperature to 1000° C. and keeping the temperature for 1 hour.

Comparative Example A1

A conventionally used highly reactive iron powder for an exothermic composition (with a bulk density of 2.0 g/cm$^3$, an average particle size of 45 µm, a BET specific surface area of 2.80 m$^2$/g, and a metal iron content of 76% by mass) was used as Comparative Example A1.

Comparative Examples A2 and A3

A general-purpose iron powder for an exothermic composition (with a bulk density of 2.9 g/cm$^3$, an average particle size of 127 µm, a BET specific surface area of 0.17 m$^2$/g, and a metal iron content of 94% by mass) was used as Comparative Example A2. Furthermore, an iron powder obtained by milling the iron powder of Comparative Example A2 using a roller mill RM36 manufactured by Kotobuki Engineering & Manufacturing Co., Ltd. was used as Comparative Example A3.

Comparative Example A4

A pure iron (atomized iron powder—180 µm manufactured by Wako Pure Chemical Industries, Ltd.) was used as Comparative Example A4.

Preparation of Coating Material

Coating materials were prepared using the iron powders of the above-described examples and comparative examples. The composition of each coating material was set so as to contain 100 parts by mass of iron powder, 8 parts by mass of carbon material (activated carbon), 0.3 parts by mass of thickener (guar gum), 60 parts by mass of water, and 5 parts by mass of electrolyte (sodium chloride). The coating material was prepared by, first, mixing the iron powder and the carbon material, adding a mixed liquid of the water and the thickener to the mixture, and uniformly mixing the resultant substance.

Production of Exothermic Body

Exothermic bodies having a configuration similar to that of the exothermic body 2 shown in FIG. 1(c) were prepared using the coating materials prepared using the iron powders of the above-described examples and comparative examples. Paper made of wood pulp fibers with a basis weight of 70 g/m$^2$ was used as the base material sheet 21, and a super absorbent sheet described below with a basis weight of 80 g/m$^2$ was used as the base material sheet 22. A coat layer was formed by uniformly coating one face of the base material sheet 21 with the coating material, a powder of a halide salt (sodium chloride) was uniformly added to the entire coat layer, and then the base material sheet 22 was overlaid thereon, and thus an exothermic body having a configuration similar to that of the exothermic body 2 was produced. In the exothermic composition, the content of the halide salt was set to 5 parts by mass with respect to 100 parts by mass of the iron powder in the exothermic composition. In the exothermic body, the basis weight of the exothermic composition was 587 g/m$^2$.

Preparation of Super Absorbent Sheet

The super absorbent sheet used as the base material sheet 22 was prepared using the method described in the specification of Japanese Patent No. 5894747. This super absorbent sheet is one sheet having a configuration in which particles of a sodium polyacrylate-based superabsorbent polymer were present mainly at substantially the center in the thickness direction of the sheet, and were not substantially present on the surfaces of the sheet. The super absorbent sheet had layers of hydrophilic cross-linked high-volume cellulose fibers on the front and back sides sandwiching the region with superabsorbent polymer particles therebetween. The cross-linked high-volume cellulose fibers had a fiber roughness of 0.22 mg/m and an average fiber length of 2.5 mm. The layers of the cross-linked high-volume cellulose fibers further contained softwood bleached kraft pulp and a paper strength agent (PVA). The superabsorbent polymer particles that were used had an average particle size of 340 µm. The superabsorbent polymer particles had a basis weight of 30 g/m$^2$, and the super absorbent sheet, that is, the base material sheet 22 had a basis weight of 80 g/m$^2$.

Evaluation Test

The preservation stabilities (handle abilities) of the coating materials prepared using the iron powders of the above-described examples and comparative examples were evaluated using the following method. Furthermore, the exothermic properties of the exothermic bodies produced using the coating material were evaluated using the following method. Table 1 below shows the results.

Method for Evaluating Preservation Stability of Coating Materials

The preservation stability of each coating material was evaluated through comparison between the solid content of the coating material immediately after production and the solid content after the coating material immediately after production was allowed to stand for 24 hours. The solid content of the coating material was evaluated by removing moisture of the coating material through heating and measuring the remaining mass. For example, 1 g of coating material was dried at 120° C. for 30 minutes, and the remaining mass was measured using a moisture analyzer HR83 manufactured by Mettler Toledo. The solid content immediately after production was evaluated such that, if the solid content after being allowed to stand for 24 hours does not change, it was evaluated as Good, and, if the solid content after 24 hours changes by 2% or more, it was evaluated as Not Good (NG). The preservation stability of the coating material is closely related to the handleability, and thus a coating material with high preservation stability can be evaluated as being excellent in terms of handleability, and being easy to handle and excellent in terms of coating suitability.

Method for Evaluating Exothermic Properties of Exothermic Bodies

The temperature measurement was performed using the temperature measurement method for disposable body warmers as defined by JIS S4100. Each obtained exothermic warmer was inserted into a bag made of a needle-punched nonwoven fabric with a basis weight of 100 g/m² and placed on an incubator at 40° C., and the exothermic properties were evaluated. This bag was formed in the shape of a bag by sealing three sides of needle-punched nonwoven fabrics. A thermometer was arranged between the exothermic warmer and the incubator surface. The exothermic warmer was arranged such that its sheet-like cover on the non-skin side was oriented toward the thermometer. The exothermic properties were evaluated by comparing areas (K·min) obtained by plotting changes in the temperature relative to the time and integrating the region with a temperature of over 45° C. with the time. Those with an area over 300 K·min, which is about twice the value 156 K·min of an existing highly reactive iron powder for an exothermic composition shown in Comparative Example A1, were taken as Good, and those with an area lower than or equal to 300 K·min were taken as NG.

invention has a bulk density in a relatively low range of 0.3 to 1.5 g/cm³, and thus, in order to increase the coating ability by making the exothermic composition using this iron powder flowable, it is necessary to increase the amount of water used together therewith to an amount larger than usual. However, if the amount of water is too large, the exothermic properties of the exothermic composition (exothermic body) may deteriorate. Regarding such an issue unique to a case in which an exothermic composition containing an oxidizable metal (an iron powder for an exothermic composition) with a low bulk density is used to form a coating material, the second aspect of the invention solves this issue by devising a step of producing an exothermic body as described below.

Figure 3:
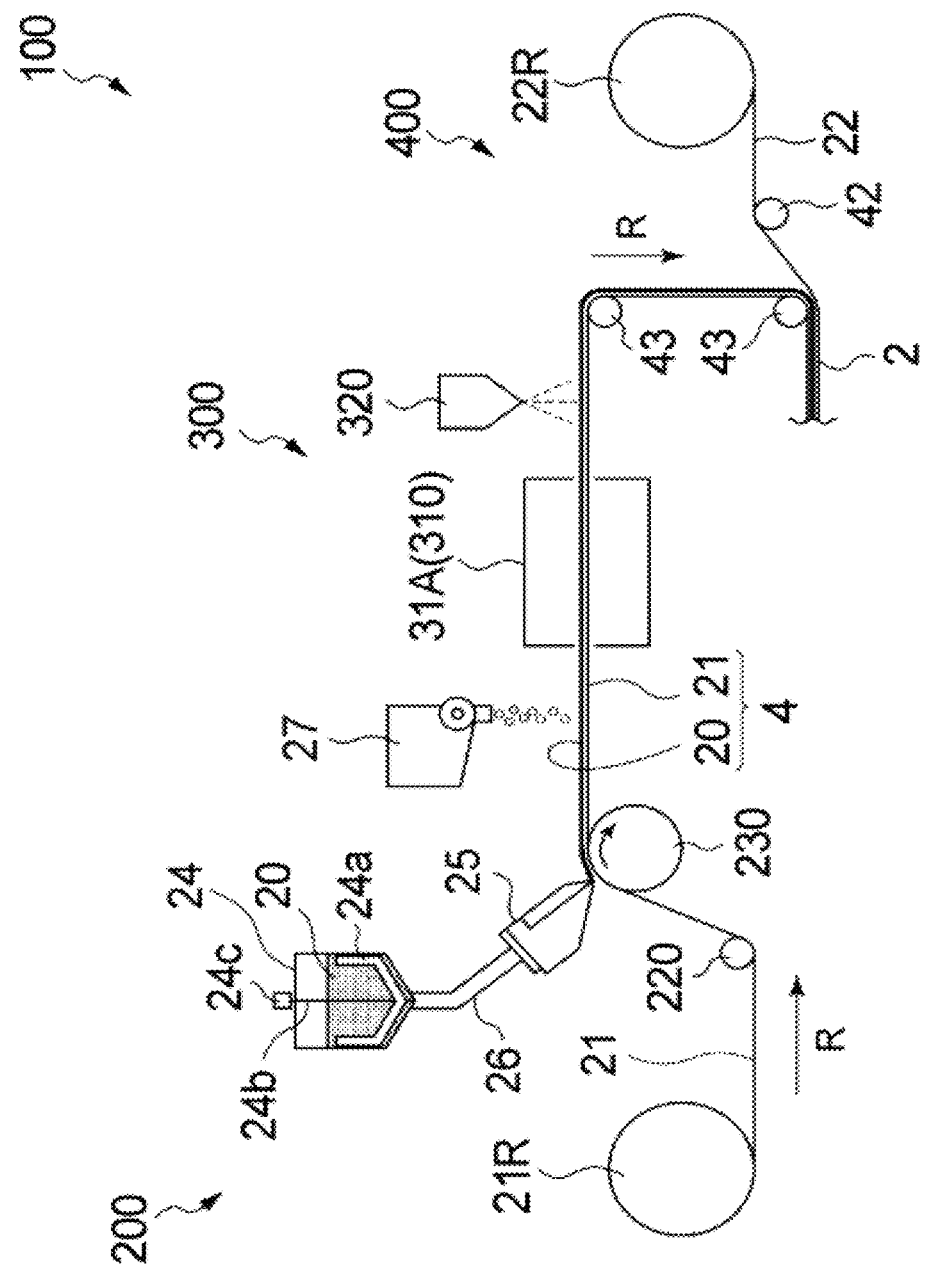
FIG. 3 is a schematic view showing a production apparatus preferably used for the present invention (the second aspect of the invention).

The exothermic body 2 according to the second aspect of the invention can be preferably produced, for example, using a production apparatus 100 shown in FIGS. 3 and 4. The production apparatus 100 shown in FIGS. 3 and 4 is roughly divided into a coated member forming portion 200, a moisture adjusting portion 300, and a sheet overlaying portion 400.

As shown in FIGS. 3 and 4, the production apparatus 100 includes the coated member forming portion 200. The coated member forming portion 200 includes a guide roller 220 and a receiving roller 230 that guide a base material sheet 21 from a web roller 21R in a conveying direction R, a storage tank 24 that stores the exothermic composition 20, which will be described later, a coating head 25 that applies the exothermic composition 20 to one face of the base material sheet 21, a supply path 26 that supplies the exothermic composition 20 from the storage tank 24 to the coating head 25, and a salt spraying apparatus 27 that sprays a salt onto a formed coated member 4.

TABLE 1

|  |  | Example A | | | Comparative Example A | | | |
| --- | --- | --- | --- | --- | --- | --- | --- | --- |
|  |  | 1 | 2 | 3 | 1 | 2 | 3 | 4 |
| Iron powder | Bulk density (g/cm³) | 1.2 | 0.7 | 0.4 | 2.0 | 2.9 | 2.9 | 3.3 |
|  | Average particle size (μm) | 50 | 55 | 70 | 45 | 127 | 15 | 84 |
|  | BET specific surface area (m²/g) | 1.70 | 2.36 | 2.94 | 2.80 | 0.17 | 0.54 | 0.05 |
|  | Pore volume as    Total pore volume | 0.63 | 0.70 | 2.52 | 0.24 | 0.17 | 0.22 | 0.16 |
|  | measured using mercury  1 μm or more | 0.56 | 0.66 | 2.43 | 0.22 | 0.17 | 0.20 | 0.16 |
|  | intrusion method (cm³/g) |  |  |  |  |  |  |  |
|  | Metal iron content (mass %) | 81 | 83 | 93 | 76 | 94 | 92 | 95 |
| Evaluation | Preservation stability of coating | Good | Good | Good | Good | NG | NG | NG |
|  | Solid concentration | 64/64 | 64/64 | 64/64 | 64/64 | 64/45 | 64/40 | 64/50 |
|  | (mass %, after production/24 hours) |  |  |  |  |  |  |  |
|  | Exothermic properties of exothermic body | Good | Good | Good | NG | NG | NG | NG |
|  | Amount of heat generated | 529 | 411 | 380 | 156 | — | 264 | 141 |
|  | (K · min) |  |  |  |  |  |  |  |

Hereinafter, the second aspect of the invention will be described based on preferred embodiments with reference to the drawings. The exothermic body production method according to the second aspect of the invention uses a flowable exothermic composition containing an oxidizable metal with a bulk density in a predetermined low range, a carbon material, and water. The exothermic composition used in the second aspect of the invention and components contained in the exothermic composition will be described later in detail.

Specific examples of the oxidizable metal used in the second aspect of the invention include the iron powder for an exothermic composition according to the first aspect of the invention. As described above, the iron powder for an exothermic composition according to the first aspect of the The storage tank 24 included in the coated member forming portion 200 stores the exothermic composition 20. The exothermic composition 20 in the storage tank 24 is made uniform through stirring by a stirring blade 24a. The stirring blade 24a is connected via a shaft 24b to a rotational drive source 24c. One end of the supply path 26 is connected to the bottom of the storage tank 24. The other end of the supply path 26 is connected to the coating head 25.

The coated member forming portion 200 includes the coating head 25. The coating head 25 is a portion that applies the flowable exothermic composition 20 that has been supplied from the storage tank 24 via the supply path 26, to one face of the continuous base material sheets 21 supported by the receiving roller 230, thereby forming a coated member 4. The coating head 25 can apply the exothermic composition 20 throughout the width direction of the base material sheet 21, which is a direction orthogonal to the conveying direction R. As the coating head 25, those that can apply a fluid, such as a die coater, are used.

It is preferable that, as shown in FIGS. 3 and 4, the coated member forming portion 200 further includes the salt spraying apparatus 27. The salt spraying apparatus 27 is a portion that sprays a salt to the exothermic composition 20 side of the formed coated member 4. The salt spraying apparatus 27 can spray a salt throughout the width direction of the coated member 4, which is a direction orthogonal to the conveying direction R.

The production apparatus 100 includes the moisture adjusting portion 300. The moisture adjusting portion 300 includes a water removing portion 310 that removes water from the coated member 4, and a water adding portion 320 that is positioned downstream of the water removing portion 310 and adjusts the water content of the coated member 4.

The water removing portion 310 is a portion that removes water from the coated member 4 that is wet, through drying, water absorption, or the like. There is no particular limitation on the form or method of the water removing portion 310, as long as desired moisture can be removed from the coated member 4. For example, the water removing portion 310 shown in FIG. 3 includes a drier 31A that dries the coated member 4 that has been guided into the drier 31A and removes water through volatilization or evaporation. In the embodiment shown in FIG. 3, only one drier 31A is provided, but it is also possible that a plurality of the driers 31A are provided along the conveying direction R. If a plurality of the driers 31A are provided, the drying temperatures at the driers 31A may be the same or may be different from each other.

Furthermore, the water removing portion 310 shown in FIG. 4 includes an absorbent roller 31B in which a portion that comes into contact with a material from which water is to be absorbed (the coated member 4) contains an absorbent material that can absorb water, instead of the drier 31A. The axial direction of the absorbent roller 31B matches the width direction of the coated member 4, and has a width that is greater than or equal to the width of the coated member 4. The absorbent roller 31B comes into contact with the coated member 4, and removes water contained in the coated member 4 through water absorption. The absorbent roller 31B may be, for example, a roller in which a circumferential face portion (outer circumferential portion) of the absorbent roller 31B, which is a portion that comes into contact with a material from which water is to be absorbed (the coated member 4), is made of an absorbent material such as sponge or pulp paper. An auxiliary roller 31C is arranged at a position facing the absorbent roller 31B. It is also possible that the auxiliary roller 31C is a belt conveyor instead of being a roller.

The water adding portion 320 is a portion that adds water to the coated member 4 from which moisture has been removed by the water removing portion 310, thereby adjusting the amount of moisture in the coated member 4. It is preferable that, as in the case of the coating head 25 and the salt spraying apparatus 27, the water adding portion 320 can add water throughout the width direction of the coated member 4. Note that, if the coated member 4 that has passed through the water removing portion 310 has a desired amount of moisture, the water adding portion 320 does not have to be provided. The amount of moisture that allows the coated member 4 to preferably exert its exothermic properties will be described later.

As shown in FIGS. 3 and 4, the production apparatus 100 includes the sheet overlaying portion 400. The sheet overlaying portion 400 includes a guide roller 42 that guides a continuous second base material sheet 22 that has been released from a second web roller 22R, to the downstream side, and a guide roller 43 that guides the coated member 4 in the conveying direction R. The second base material sheet 22 is conveyed so as to be located on the face of the coated member 4, on the exothermic composition 20 side.

The production apparatus 100 shown in FIGS. 3 and 4 was described above. Hereinafter, a preferred method for producing an exothermic body according to the second aspect of the invention using the production apparatus 100 will be described.

First, the exothermic composition 20 containing an oxidizable metal with a bulk density in a predetermined range, a carbon material, and water is filled into the storage tank 24. The oxidizable metal is typically the iron powder for an exothermic composition according to the first aspect of the invention. The exothermic composition 20 may be an exothermic composition that has been prepared in advance using another stirring apparatus (not shown) and be filled into the storage tank 24, or may be prepared by placing an oxidizable metal, a carbon material, and water into the storage tank 24, and stirring and mixing them. Since the exothermic composition 20 has a large amount of moisture, a flowable coating material (slurry-like exothermic composition) is obtained. From the viewpoint of suppressing sedimentation of components of the exothermic composition 20 and maintaining uniformity, it is preferable that the exothermic composition 20 is stirred during supply.

Next, in a state in which the base material sheet 21 released from the web roller 21R is positioned on the circumferential face of the receiving roller 230, the coating head 25 applies the exothermic composition 20 to the base material sheet 21. Since the exothermic composition 20 is continuously supplied from the storage tank 24 via the supply path 26 to the coating head 25, the exothermic composition 20 is applied to the base material sheet 21 along the conveying direction R in a continuous manner in accordance with conveyance of the base material sheet 21 in the conveying direction R. Accordingly, the coated member 4 in which the upper face of the base material sheet 21 is coated with the exothermic composition 20 is continuously formed and is conveyed to the downstream side. In this step, the exothermic composition 20 is a flowable coating material (slurry-like exothermic composition).

Next, as shown in FIGS. 3 and 4, the salt spraying apparatus 27 positioned downstream of the coating head 25 sprays a salt onto the exothermic composition 20 side of the coated member 4. Through this step, the exothermic properties resulting from an oxidation reaction of the oxidizable metal of the exothermic body can be further improved. As described above, if the iron powder for an exothermic composition according to the first aspect of the invention is used as the oxidizable metal, it is preferable to use a halide salt as the salt. Since the salt spraying apparatus 27 is positioned above the coated member 4, on the side of a face coated with the exothermic composition 20, the salt is applied to the upper face of the exothermic composition 20 in the coated member 4 along the conveying direction R in a continuous manner. From the viewpoint of suppressing issues such as corrosion of the production apparatus and dispersion of the salt to the surrounding area of the production apparatus, it is preferable to spray the salt in a solid state. The salt sprayed in a solid state is conveyed to the downstream in a state in which part of or the whole salt is dissolved in water contained in the exothermic composition 20. Also in this step, the exothermic composition 20 is a flowable coating material (slurry-like exothermic composition).

Subsequently, as shown in FIGS. 3 and 4, the coated member 4 is supplied to the water removing portion 310 positioned downstream of the salt spraying apparatus, so that water is removed from the coated member 4. Since the oxidizable metal contained in the exothermic composition 20 has a bulk density in a low range of 0.3 to 1.5 g/cm$^3$, moisture is likely to be retained in voids in metal particles and between metal particles. Accordingly, when forming the coated member 4, it is necessary to make the amount of moisture that is to be added when producing the exothermic composition 20 larger than an optimal amount, thereby ensuring the flowability of the exothermic composition 20. On the other hand, if the amount of moisture in the exothermic composition 20 is excessive, an oxidation reaction of the oxidizable metal is inhibited by the presence of water, the heat capacity of the exothermic body increases, and it is difficult to obtain desired exothermic properties of the exothermic body. This step is performed in order to decrease the amount of moisture in the coated member 4 toward an optimal amount, and maintain a stable exothermic reaction resulting from an oxidation reaction of the oxidizable metal for a long period of time.

As shown in FIG. 3, in the embodiment using the drier 31A in the water removing portion 310, the coated member 4 is supplied into the drier 31A and dried, and water contained in the exothermic composition 20 constituting the coated member 4 is removed through volatilization or evaporation. There is no particular limitation on the method for drying the coated member 4 in the drier 31A, as long as water can be removed from the coated member 4, and examples thereof include blowing of hot air, blowing of dried gas, heating with a heater, irradiation of infrared rays, and heating with application of heat and pressure using a hot roller. In this embodiment, part of water contained in the coated member 4 may be removed, or the whole water may be removed. That is to say, the coated member 4 may be kept wet, or may be absolutely dried. If part of water contained in the coated member 4 is removed, it is preferable to remove water such that the amount of moisture contained in the coated member 4 after the removal is less than or equal to the amount of moisture contained in the finally obtained exothermic body.

From the viewpoint of suppressing an unintended oxidation reaction of the oxidizable metal, the atmosphere for the coated member 4 during drying is preferably an atmosphere with an inert gas such as nitrogen or argon. The drying temperature of the coated member 4 depends on constituent components of the base material sheet 21 and the exothermic composition 20 constituting the coated member 4, but it is preferably 10° C. or more, and more preferably 30° C. or more, and is preferably 300° C. or less, and more preferably 100° C. or less. The drying time of the coated member 4 depends on the drying temperature or a target amount of moisture but, it is preferably 2 minutes or more, and more preferably 10 minutes or more, and is preferably 180 minutes or less, and more preferably 120 minutes or less.

As shown in FIG. 4, in the embodiment using the absorbent roller 31B made of an absorbent material as the water removing portion 310, the coated member 4 is supplied to a point between the absorbent roller 31B and the auxiliary roller 31C and is brought into contact with the absorbent material, so that water is removed from the coated member 4 through water absorption. In this embodiment, it is difficult to absorb the whole water contained in the coated member 4, and thus the coated member 4 is conveyed to the downstream side while being kept wet. In this case, it is preferable to remove water such that the amount of moisture contained in the coated member 4 after removal of water is less than or equal to the amount of moisture contained in the finally obtained exothermic body.

From the viewpoint of the efficiency of removal of water through absorption, it is preferable that the absorbent material that is brought into contact with the coated member 4 is a material such as polyvinyl alcohol, urethane, or pulp paper. Furthermore, from similar viewpoints, it is preferable that the coated member 4 is brought into contact with the absorbent material at least from the exothermic composition 20 side of the coated member 4. From the viewpoint of the efficiency of removal of water through absorption, the pressing pressure (pressing line pressure) in a case in which the absorbent material is used in the form of the absorbent roller 31B as shown in FIG. 4 is preferably 0.5 N/m or more, and more preferably 1.5 N/m or more. From the viewpoint of suppressing adhesion of the exothermic composition 20 to the absorbent roller 31B, and easily performing machine maintenance, the pressing pressure is preferably 300 N/m or less, and more preferably 50 N/m or less. From the viewpoint of removing moisture through absorption while suppressing adhesion of the exothermic composition 20 to the absorbent roller 31B, it is preferable that another water-permeable sheet (not shown) such as a water-permeable fibrous sheets or mesh sheet is provided between the absorbent roller 31B and the exothermic composition 20.

The amount that is "less than or equal to the amount of moisture contained in the finally obtained exothermic body, which is the amount of moisture in the coated member 4 after removal of water by the water removing portion 310" is preferably from 0 to 110 parts by mass, and more preferably from 0 to 100 parts by mass, with respect to 100 parts by mass of the oxidizable metal. The amount of moisture in the coated member 4 after removal of water can be measured, for example, according to the method as defined by JIS K 0068:2001. Furthermore, the amount of moisture in the coated member 4 after removal of water can be obtained by calculating a difference between the basis weight of the coated member 4 formed through application by the coating head to one face of the base material sheet 21 and the basis weight of the coated member 4 after removal of water. Furthermore, the amount of moisture in the coated member 4 after removal of water can be obtained through inline measurement using an infrared moisture meter, a near-infrared moisture meter, or a microwave transmission-type moisture meter.

Subsequently, as shown in FIGS. 3 and 4, the water adding portion 320 positioned downstream of the water removing portion 310 adds water to the coated member 4, from the side of a face coated with the exothermic composition 20. In FIGS. 3 and 4, water is sprayed from the water adding portion 320 onto the exothermic composition 20 of the coated member 4, thereby adding water to the coated member. It is preferable that the amount of moisture contained in the coated member 4 after water is added is equal to the amount of moisture contained in the finally obtained exothermic body. Through this step, even when water is excessively removed from the coated member 4 by the water removing portion 310, the amount of moisture can be adjusted to an amount that allows an oxidation reaction of the oxidizable metal to sufficiently progress. Note that, if the amount of moisture in the coated member 4 that has passed through the water removing portion 310 is within a later-described range, water does not have to be added by the water adding portion 320.

Through this step, the coated member 4 is conveyed to the downstream side while the amount of moisture contained therein is adjusted to an optimal amount that is preferably 30 parts by mass or more, and more preferably 40 parts by mass or more, and is preferably 110 parts by mass or less, and more preferably 100 parts by mass or less, with respect to 100 parts by mass of the oxidizable metal. If the amount of moisture in the coated member 4 is adjusted to this range, an oxidation reaction of the oxidizable metal can be allowed to sufficiently progress, and a stable exothermic reaction can be maintained for a long period of time. As a result, the exothermic properties of the exothermic body become excellent.

Lastly, the second base material sheet 22 released from the second web roller 22R is overlaid on the exothermic composition 20 side of the coated member 4, and thus the exothermic body 2 as shown in FIG. 1(c) is produced. It is also possible to perform crimping using a crimping means (not shown) such as a nip roller as necessary. Note that the above-described optimal amount of moisture in the coated member 4 is maintained also during production of the exothermic body 2, and thus the above-described optimal amount of moisture in the coated member 4 is substantially the same as the amount of moisture in the coated member 4 in the finally obtained exothermic body 2. Furthermore, the above-described optimal amount of moisture in the coated member 4 is substantially the same as the amount of moisture contained in the finally obtained exothermic body 2.

As shown in FIG. 1(c), the exothermic body 2 produced through these production steps has a structure in which an exothermic layer containing the exothermic composition 20 as a raw material is arranged between the base material sheet 21 and the second base material sheet 22. As the material constituting the base material sheets 21 and 22, it is possible to use sheets conventionally used in conventional techniques, and examples thereof include air-impermeable materials such as synthetic resin films, air-permeable materials made of fibrous sheets such as nonwoven fabrics or paper, laminates of the air-impermeable materials and the fibrous sheets, and the like. Furthermore, the base material sheets 21 and 22 may have water-absorbing properties, and examples thereof include fibrous sheets containing hydrophilic fibers, fibrous sheets containing absorbent polymer particles and hydrophilic fibers, and the like. The base material sheets 21 and 22 may be made of the same material, or may be made of different materials. From the viewpoint of maintaining an exothermic reaction of the exothermic body resulting from an oxidation reaction, it is preferable that at least one of the base material sheets 21 and 22 is air-permeable.

From the viewpoint of preventing permeation of water when forming the coated member 4, it is preferable to use, as the base material sheet 21, a laminate of an air-impermeable material such as a synthetic resin film and a fibrous sheet such as a nonwoven fabric or paper containing hydrophilic fibers but not containing absorbent polymers. From the viewpoint of easily adjust the amount of moisture in the exothermic composition 20 such that an exothermic reaction is allowed to occur, it is preferable to use, as the second base material sheet 22, a fibrous sheet containing absorbent polymers (super absorbent sheet). The absorbent polymer content in the super absorbent sheet is usually approximately 10 to 70% by mass with respect to the total mass of the super absorbent sheet.

The basis weights of the base material sheets 21 and 22 are each independently preferably 10 $g/m^2$ or more, and more preferably 20 $g/m^2$ or more, and are each independently preferably 300 $g/m^2$ or less, and more preferably and more preferably 200 $g/m^2$ or less. Furthermore, the basis weight of the exothermic composition 20 in the exothermic body 2 is preferably 50 $g/m^2$ or more, and more preferably 100 $g/m^2$ or more, and is preferably 2500 $g/m^2$ or less, and more preferably 2000 $g/m^2$ or less.

The exothermic body 2 produced according to the second aspect of the invention can be used as an exothermic warmer such as a disposable body warmer, as is, or in a state in which the entire exothermic body 2 is covered by or enclosed in a package member such as an air-permeable porous sheet. The exothermic warmer to which the second aspect of the invention can be applied is the same as the exothermic warmer to which the first aspect of the invention can be applied. Furthermore, the outer face of the package member may be coated with a known adhesive in order to fix the exothermic warmer to the contact region.

The exothermic body production method according to the second aspect of the invention was described above. Hereinafter, an exothermic composition preferably used in the production of an exothermic body according to the second aspect of the invention will be described. The exothermic composition used in the production of an exothermic body according to the second aspect of the invention contains an oxidizable metal, a carbon material, and water, and is flowable.

The exothermic composition used in the production of an exothermic body according to the second aspect of the invention contains an oxidizable metal. The oxidizable metal in this specification is a metal that oxidizes by reacting with oxygen in air and generates heat. Examples of the oxidizable metal include iron, aluminum, zinc, manganese, magnesium, calcium, and the like, which may be used alone or in combination of two or more. From the viewpoint of handleability, safety, production cost, and preservation stability, the oxidizable metal preferably contains iron as a main component, and, from the viewpoint of ensuring the reactivity of the oxidation reaction and the flowability of the exothermic composition, the oxidizable metal is preferably in the form of a granule or a powder. From the viewpoint of preferably achieving these advantages, iron in the form of a powder, that is, an iron powder is particularly preferably used. Examples of the iron powder include a reduced iron powder, an atomized iron powder, and the like.

If an oxidizable metal containing iron as a main component is used, the metal iron content in the oxidizable metal is preferably 60% by mass or more, and more preferably 70% by mass or more, and the upper limit thereof is preferably 95% by mass or less, and more preferably 90% by mass or less. If the metal iron content in the oxidizable metal is within this range, the exothermic body can more reliably exert its exothermic properties. The metal iron content in the oxidizable metal can be measured, for example, using the bromine-methanol titrimetric method as defined by ISO5416.

The bulk density of the oxidizable metal contained in the exothermic composition is preferably 0.3 $g/cm^3$ or more, and more preferably 0.4 $g/cm^3$ or more, and the upper limit thereof is preferably 1.5 $g/cm^3$ or less, and more preferably 1.4 $g/cm^3$ or less. Specifically, the bulk density of the oxidizable metal is preferably from 0.3 to 1.5 $g/cm^3$, and more preferably from 0.4 to 1.4 $g/cm^3$. If an oxidizable metal with this bulk density is used in the exothermic composition, the reaction ratio of the oxidation reaction of the oxidizable metal is improved, and thus the exothermic properties of the exothermic body can be improved. The bulk density of the oxidizable metal can be measured, for example, using a bulk density measuring device (JIS bulk specific gravity measuring device, manufactured by Tsutsui Rikagaku Kikai Co., Ltd.) according to JIS Z 2504:2012. It can be assured that a particle with a lower bulk density has a higher volume.

If a granule or a powder is used as the oxidizable metal contained in the exothermic composition, the average particle size thereof is preferably 10 μm or more, and more preferably 20 μm or more, and the upper limit thereof is preferably 150 μm or less, and more preferably 100 μm or less. Specifically, the average particle size of the oxidizable metal is preferably from 10 to 150 μm, and more preferably from 20 to 100 μm. If an oxidizable metal with this average particle size is used in the exothermic composition, the exothermic properties of the exothermic body can be improved, and the thickness of the exothermic body can be reduced.

As the average particle size of the oxidizable metal, for example, a volume-based median diameter as measured using a laser diffraction particle size distribution analyzer is used. If an iron powder is used as the oxidizable metal, for example, a method is used in which a measurement is performed using an LA-950V2 manufactured by Horiba, Ltd. with a standard wet circulation cell with settings in which the refractive index of an iron powder is 3.5 for the real part and 3.8i for the imaginary part, water is used as a dispersion medium and the refractive index thereof is 1.33, the circulation speed is 15, and the agitation is 5, and the thus obtained volume-based median diameter is taken as a measurement result of the average particle size of an iron powder.

The BET specific surface area of the oxidizable metal contained in the exothermic composition 20 is preferably 0.1 $m^2/g$ or more, and more preferably 0.2 $m^2/g$ or more, and the upper limit thereof is preferably 50 $m^2/g$ or less, and more preferably 40 $m^2/g$ or less. If the BET specific surface area of the oxidizable metal is within this range, the activity of the oxidation reaction of the oxidizable metal increases, and thus the exothermic properties of the exothermic body can be improved. The BET specific surface area of an oxidizable metal can be measured, for example, using a known BET method. The BET method is a method in which the specific surface area of a powder is measured by measuring the amount of nitrogen, argon, or the like adsorbed to the powder surface.

The pore volume of the oxidizable metal contained in the exothermic composition as measured using the mercury intrusion method, in a range of 1 μm or more, is preferably 0.3 $cm^3/g$ or more, and more preferably 0.5 $cm^3/g$ or more, and the upper limit thereof is preferably 4.0 $cm^3/g$ or less, and more preferably 3.0 $cm^3/g$ or less. Furthermore, under a condition that the pore volume of the oxidizable metal as measured using the mercury intrusion method, in a range of 1 μm or more, is within the above-described specific range, the total pore volume of the oxidizable metal is preferably 0.3 $cm^3/g$ or more, and more preferably 0.5 $cm^3/g$ or more, and the upper limit thereof is preferably 4.0 $cm^3/g$ or less, and more preferably 3.0 $cm^3/g$ or less. If the pore volume of the oxidizable metal as measured using the mercury intrusion method is within this range, the activity of the oxidation reaction of the oxidizable metal increases, and the exothermic properties of the exothermic body can be improved. The pore volume as measured using the mercury intrusion method can be measured, for example, according to the method as defined by JIS R 1655:2003.

The oxidizable metal (iron powder for an exothermic composition) in the form of a powder containing iron as a main component, and satisfying the above-described average particle size, BET specific surface area, and pore volume as measured using the mercury intrusion method, which is a preferred embodiment of the oxidizable metal used in the second aspect of the invention, can be produced as follows. For example, the oxidizable metal can be obtained by performing reduction treatment on iron ore containing iron oxide (III) that is a raw material, using a solid reductant in a reducing furnace such as a rotary kiln thereby obtaining reduced iron, milling the reduced iron using a mill, and, as necessary, sieving the resultant substance into particles with a desired particle size. In particular, in the case of milling the reduced iron, it is preferable that the milling level is lowered. Specifically, for example, it is preferable that milling is performed on 0.05 kg of reduced iron for approximately 5 to 30 seconds at a number of rotations of 700 to 1000 rpm using a vibratory disc mill (e.g., product name "RS200" manufactured by Verder Scientific Co., Ltd.). If such milling is performed, an oxidizable metal (iron powder for an exothermic composition) in the form of a powder satisfying the above-described average particle size, BET specific surface area, and pore volume as measured using the mercury intrusion method can be easily obtained.

The metal iron content in the oxidizable metal can be adjusted by modifying the reducing conditions, the heating conditions after reduction, and the like as appropriate. Furthermore, the average particle size of the oxidizable metal, the BET specific surface area, and the pore volume as measured using the mercury intrusion method can be adjusted by adjusting the milling level in the milling as appropriate.

Note that the oxidizable metal may contain, as other components, for example, approximately 3% by mass or less of silica ($SiO_2$), approximately 15% by mass or less of carbon (C), and approximately 3% by mass or less of alumina ($Al_2O_3$). Since an oxidizable metal inevitably oxidizes by reacting with the oxygen in air at room temperature also during production, the oxidizable metal may contain approximately 10% by mass or less of oxygen (O). These other components are inevitably mixed mainly in a step of producing an oxidizable metal.

As a preferred example of the oxidizable metal used in the second aspect of the invention, the iron powder for an exothermic composition according to the first aspect of the invention described above is conceivable.

The exothermic composition used in the production of an exothermic body according to the second aspect of the invention contains a carbon material. The carbon material contained in the exothermic composition has at least one of a water-retaining ability, an oxygen-retaining ability, an oxygen-supplying ability, and a catalytic ability, and preferably has all of these functions. Examples of the carbon material having such functions include activated carbon, acetylene black, black lead, graphite, coal, and the like, which may be used alone or in combination of two or more. Of these carbon materials, it is preferable to use activated carbon as the carbon material from the viewpoint of allowing the carbon material to sufficiently exert its water-retaining ability, oxygen-retaining ability, and oxygen-supplying ability, resulting from a high specific surface area. Examples of the activated carbon that can be used as the carbon material include a powder or a granule of coconut shell carbon, charcoal powder, and peat carbon, or the like.

The carbon material content in the exothermic composition is preferably 3 parts by mass or more, and more preferably 5 parts by mass or more, and the upper limit thereof is preferably 30 parts by mass or less, and more preferably 25 parts by mass or less, with respect to 100 parts by mass of the oxidizable metal in the exothermic composition. If the carbon material content is within this range, the oxidation reaction efficiency of the oxidizable metal can be maintained for a long period of time. As a result, the exothermic body can sufficiently exert its exothermic properties.

The exothermic composition used in the production of an exothermic body according to the second aspect of the invention contains water. The water can be used in an oxidation reaction of the oxidizable metal and is used also as a coolant for cooling generated heat to an appropriate temperature. If an oxidizable metal with a low bulk density, for example, the iron powder for an exothermic composition according to the first aspect of the invention is used as a raw material in production of an exothermic body, moisture is likely to be retained in voids in raw material particles and between raw material particles, and thus it is necessary to ensure flowability suitable for coating, by increasing the amount of moisture that is to be added during production of the exothermic composition, to an amount larger than usual.

From the viewpoint of improving the coating ability by ensuring the flowability of the exothermic composition, the water content in the exothermic composition is preferably 70 parts by mass or more, and more preferably 80 parts by mass or more, and the upper limit thereof is preferably 160 parts by mass or less, and more preferably 150 parts by mass or less, with respect to 100 parts by mass of the oxidizable metal in the exothermic composition. If water is contained in this range in the exothermic composition, the exothermic composition is a flowable coating material (slurry-like exothermic composition).

From the viewpoint of increasing the oxidation reaction efficiency of the oxidizable metal and maintaining an oxidation reaction of the oxidizable metal, the exothermic composition used in the production of an exothermic body according to the second aspect of the invention may further contain a salt. If a salt is contained in the exothermic composition, it is dissolved in water. Examples of the salt include chlorides such as sodium chloride, potassium chloride, calcium chloride, and magnesium chloride, sulfates such as sodium sulfate and potassium sulfate, phosphates such as trisodium phosphate and tripotassium phosphate, and hydroxides such as sodium hydroxide and potassium hydroxide. These salts may be used alone or in combination of two or more. If the iron powder for an exothermic composition according to the first aspect of the invention described above is used as the oxidizable metal, it is preferable to use a halide salt as the salt. As the halide salt that is used in the second aspect of the invention, it is possible to use those that can be used in the first aspect of the invention. The salt content in the exothermic composition is preferably 2 parts by mass or more, and more preferably 3 parts by mass or more, and the upper limit thereof is preferably 30 parts by mass or less, and more preferably 25 parts by mass or less, with respect to 100 parts by mass of the oxidizable metal in the exothermic composition.

The exothermic composition may contain, in addition to the oxidizable metal, the carbon material, and the water, other additives as necessary. Examples of the additives include a reaction accelerator for retaining moisture or supplying oxygen, a thickener and a surfactant for improving the coating ability of the exothermic composition, and the like. Examples of the reaction accelerator may include zeolite, pearlite, vermiculite, silica, alumina, titania, sawdust, and the like. Examples of the thickener may include substances that absorb moisture, thereby increasing the consistency or providing the thixotropy, and examples thereof include bentonite, stearate, polyacrylate such as sodium polyacrylate; gelatin, tragacanth gum, locust bean gum, guar gum, gum arabic, alginate such as sodium alginate; pectin, carboxyvinyl polymer, dextrin, starch-based absorbent such as pregelatinized starch and starch for processing; polysaccharide-based thickeners such as carrageenan and agar; cellulose derivative-based thickeners such as carboxymethylcellulose, ethylcellulose acetate, hydroxyethylcellulose, methylcellulose, and hydroxypropylcellulose, and the like. Examples of the surfactants include anionic surfactants containing, as a main component, a condensate of aromatic sulfonic acid and formalin or a special carboxylic acid-type high-molecular surfactant.

The viscosity of the exothermic composition containing the above-described components is preferably 3000 mPa·s or more, and more preferably 4000 mPa·s or more, and the upper limit thereof is preferably 18000 mPa·s or less, and more preferably 10000 mPa·s or less. If the exothermic composition has this viscosity, the exothermic composition 20 can be uniformly applied to a target coating position on the base material sheet, and thus the exothermic body 2 with uniform exothermic properties can be produced. The viscosity of the exothermic composition can be measured using a B-type viscometer TVB-10 manufactured by Toki Sangyo Co., Ltd. under measurement conditions of rotor No. 4, 6 rpm, 24° C., and 60 seconds.

There is no particular limitation on the method for producing an exothermic composition containing these components, as long as it contains an oxidizable metal, a carbon material, and water, and is flowable, and, for example, the exothermic composition can be produced by mixing an oxidizable metal, a carbon material, and water using a known stirring device.

The second aspect of the invention was described above based on an embodiment thereof, but the second aspect of the invention is not limited to the foregoing embodiment. For example, in the embodiment shown in FIGS. 3 and 4, the salt spraying apparatus 27 sprays a salt onto the coated member 4, after which the water removing portion 310 removes water, but, instead of this configuration, it is also possible that the water removing portion 310 removes water, after which the salt spraying apparatus 27 sprays a salt onto the coated member 4, and the second base material sheet 22 is overlaid thereon, so that the exothermic body 2 is produced. In particular, in the embodiment shown in FIG. 4, in a case in which the absorbent roller 31B removes water after a salt is sprayed, the salt dissolved in water may be also removed together with moisture, it is preferable that, after the water removing portion 310 removes water, the salt spraying apparatus 27 sprays a salt thereon, and, as necessary, the water adding portion 320 further adds water to the layered member containing the coated member 4.

Furthermore, in the water removing portion 310 shown in FIGS. 3 and 4, one drier 31A or one absorbent roller 31B is provided, but it is also possible that a plurality of the driers 31A or a plurality of the absorbent rollers 31B are provided along the conveying direction R. In this case, a plurality of the driers 31A may be provided, a plurality of the absorbent rollers 31B may be provided, or a plurality of them may be provided in combination.

Furthermore, the water removing portion 310 in FIG. 4 was described as a form of the absorbent roller 31B containing an absorbent material, but the form is not limited to that shown in FIG. 4, as long as an absorbent material is used, and it is also possible that, for example, instead of the absorbent roller 31B, an absorbent sponge in the shape of a rectangle or the like and made of the absorbent material is brought into surface-contact with the upper face (face on the exothermic composition 20 side of the coated member 4) of the coated member 4, and thus water is removed from the coated member 4. The pressing pressure when the coated member 4 and the absorbent material are brought into surface-contact with each other is preferably from 2000 to 600000 N/m², and more preferably from 3500 to 40000 N/m².

Furthermore, in the embodiment shown in FIGS. 3 and 4, after water is removed from the coated member 4, the second base material sheet 22 is overlaid thereon, so that the exothermic body 2 is produced, but it is also possible that the second base material sheet 22 is overlaid on the exothermic composition 20 side of the coated member 4 from which water has not been removed, after which water is removed, so that the exothermic body 2 is produced. In order to produce the exothermic body 2 after the layered member is formed, it is sufficient that, after the salt spraying apparatus 27 sprays a salt onto the coated member 4, the second base material sheet 22 is overlaid thereon, so that the layered member is formed, and then the water removing portion 310 removes water from the layered member containing the coated member 4, and, as necessary, the water adding portion 320 further adds water to the layered member containing the coated member 4. From the viewpoint of the convenience in the producing step, in a case in which water is added to the layered member containing the coated member 4, it is preferable that water is added from the second base material sheet 22 side. Even according to the exothermic body 2 produced in this manner, the exothermic properties that are effects of the second aspect of the invention can be sufficiently achieved.

Regarding the foregoing embodiment, the second aspect of the invention further discloses the following exothermic body production method.

<B1>
An exothermic body production method including the steps of: forming a coated member by coating a base material sheet with a flowable exothermic composition containing an oxidizable metal with a bulk density of 0.3 to 1.5 g/cm³, a carbon material, and water; and adjusting an amount of moisture in the coated member by removing water from the coated member.

<B2>
An exothermic body production method including the steps of: forming a coated member by coating a base material sheet with a flowable exothermic composition containing the iron powder for an exothermic composition as set forth in clause <A1> (an iron powder for an exothermic composition, with a bulk density of 0.3 to 1.5 g/cm³), a carbon material, and water; and adjusting an amount of moisture in the coated member by removing water from the coated member.

<B3>
The exothermic body production method as set forth in clause <B1> or <B2>, wherein a water content in the exothermic composition is preferably 70 parts by mass or more, and more preferably 80 parts by mass or more, and the upper limit thereof is preferably 160 parts by mass or less, and more preferably 150 parts by mass or less, with respect to 100 parts by mass of the oxidizable metal in the exothermic composition or the iron powder for an exothermic composition.

<B4>
The exothermic body production method as set forth in any one of clauses <131> to <B3>, wherein water is removed from the coated member such that an amount of moisture contained in the coated member after removal of water is less than or equal to an amount of moisture contained in the finally obtained exothermic body, and then water is added to the coated member such that the amount of moisture contained in the coated member is equal to the amount of moisture contained in the finally obtained exothermic body.

<B5>
The exothermic body production method as set forth in clause <B4>, wherein the amount that is "less than or equal to an amount of moisture contained in the finally obtained exothermic body" is preferably from 0 to 110 parts by mass, and more preferably from 0 to 100 parts by mass, with respect to 100 parts by mass of the oxidizable metal.

<B6>
The exothermic body production method as set forth in clause <B4> or <B5>, wherein water is added to the coated member from a side of a face coated with the exothermic composition.

<B7>
The exothermic body production method as set forth in any one of clauses <B1> to <B6>, wherein water is removed from the coated member through drying in an inert gas atmosphere at 10 to 300° C.

<B8>
The exothermic body production method as set forth in clause <B7>, wherein a drying temperature of the coated member is preferably 10° C. or more, and more preferably 30° C. or more, and is preferably 300° C. or less, and more preferably 100° C. or less.

<B9>
The exothermic body production method as set forth in clause <B7> or <B8>, wherein a drying time of the coated member is preferably 2 minutes or more, and more preferably 10 minutes or more, and is preferably 180 minutes or less, and more preferably 120 minutes or less.

<B10>
The exothermic body production method as set forth in any one of clauses <B1> to <B9>, wherein water is removed from the coated member through contact between the coated member and an absorbent material.

<B11>
The exothermic body production method as set forth in clause <B10>, wherein the coated member is supplied to a point between an absorbent roller in which a circumferential face portion is made of the absorbent material, and an auxiliary roller, and is brought into contact with the absorbent material, so that water is removed from the coated member through water absorption.

<B12>
The exothermic body production method as set forth in clause <B11>, wherein a pressing line pressure of the absorbent roller is preferably 0.5 N/m or more, and more preferably 1.5 N/m or more, and is preferably 300 N/m or less, and more preferably 50 N/m or less.

<B13>
The exothermic body production method as set forth in clause <B11> or <B12>, wherein, after water is removed from the coated member through the absorbent roller, a halide salt is sprayed onto the coated member.

<B14>

The exothermic body production method as set forth in clause <B10>, wherein water is removed from the coated member through surface-contact between the coated member and an absorbent sponge made of the absorbent material at a pressing pressure of preferably 2000 to 600000 N/m$^2$, and more preferably 3500 to 40000 N/m$^2$.

<B15>

The exothermic body production method as set forth in any one of clauses <B10> to <B14>, wherein it is preferable that a water-permeable sheet is provided between the absorbent material and the exothermic composition applied onto the base material sheet.

<B16>

The exothermic body production method as set forth in any one of clauses <B1> to <B15>, wherein an amount of moisture in the coated member is adjusted to an optimal amount that is preferably 30 parts by mass or more, and more preferably 40 parts by mass or more, furthermore, preferably 110 parts by mass or less, and more preferably 100 parts by mass or less, with respect to 100 parts by mass of the oxidizable metal or the iron powder for an exothermic composition.

<B17>

The exothermic body production method as set forth in any one of clauses <B1> to <B16>, wherein a basis weight of the exothermic composition in the exothermic body is preferably 50 g/m$^2$ or more, and more preferably 100 g/m$^2$ or more, and is preferably 2500 g/m$^2$ or less, and more preferably 2000 g/m$^2$ or less.

<B18>

The exothermic body production method as set forth in any one of clauses <B1> to <B17>, wherein the oxidizable metal or the iron powder for an exothermic composition contains iron as a main component, and a metal iron content in the oxidizable metal or the iron powder for an exothermic composition is preferably 60% by mass or more, and more preferably 70% by mass or more, and the upper limit thereof is preferably 95% by mass or less, and more preferably 90% by mass or less.

<B19>

The exothermic body production method as set forth in any one of clauses <B1> to <B18>, wherein a bulk density of the oxidizable metal or the iron powder for an exothermic composition is preferably 0.3 g/cm$^3$ or more, and more preferably 0.4 g/cm$^3$ or more, and the upper limit thereof is preferably 1.5 g/cm$^3$ or less, and more preferably 1.4 g/cm$^3$ or less, and, specifically, it is preferably from 0.3 to 1.5 g/cm$^3$, and more preferably from 0.4 to 1.4 g/cm$^3$.

<B20>

The exothermic body production method as set forth in any one of clauses <B1> to <B19>, wherein a granule or a powder is used as the oxidizable metal or the iron powder for an exothermic composition, and an average particle size of the oxidizable metal or the iron powder for an exothermic composition is preferably 10 μm or more, and more preferably 20 μm or more, the upper limit thereof is preferably 150 μm or less, and more preferably 100 μm or less, and, specifically, it is preferably from 10 to 150 μm, and more preferably from 20 to 100 μm.

<B21>

The exothermic body production method as set forth in any one of clauses <B1> to <B20>, wherein a BET specific surface area of the oxidizable metal or the iron powder for an exothermic composition is preferably 0.1 m$^2$/g or more, and more preferably 0.2 m$^2$/g or more, and the upper limit thereof is preferably 50 m$^2$/g or less, and more preferably 40 m$^2$/g or less.

<B22>

The exothermic body production method as set forth in any one of clauses <B1> to <B21>, wherein a pore volume as measured using a mercury intrusion method of the oxidizable metal or the iron powder for an exothermic composition, in a range of 1 μm or more, is preferably 0.3 cm$^3$/g or more, and more preferably 0.5 cm$^3$/g or more, and the upper limit thereof is preferably 4.0 cm$^3$/g or less, and more preferably 3.0 cm$^3$/g or less, and a total pore volume of the oxidizable metal or the iron powder for an exothermic composition is preferably 0.3 cm$^3$/g or more, and more preferably 0.5 cm$^3$/g or more, and the upper limit thereof is preferably 4.0 cm$^3$/g or less, and more preferably 3.0 cm$^3$/g or less.

EXAMPLES

Hereinafter, the second aspect of the invention will be described by way of examples in more detail. However, the scope of the second aspect of the invention is not limited to these examples.

Example B1

Preparation of Exothermic Composition

An exothermic composition containing an oxidizable metal, a carbon material, and water was prepared. The oxidizable metal used in this example was an iron powder for an exothermic composition (the iron powder for an exothermic composition according to the first aspect of the invention) having a bulk density of 0.6 g/cm$^3$, an average particle size of 53 μm, a BET specific surface area of 12 m$^2$/g, and a pore volume as measured using the mercury intrusion method, in a range of 1 μm or more, of 0.9 cm$^3$/g. A mixture was prepared by mixing 8 parts by mass of carbon material (activated carbon) with 100 parts by mass of the iron powder for an exothermic composition, and a target exothermic composition was prepared by further adding 114 parts by mass of water, 1.8 parts by mass of tripotassium phosphate, 0.25 parts by mass of guar gum as a thickener, and 0.47 parts by mass of 48% potassium hydroxide to the mixture, and further mixing the resultant substance. The exothermic composition was flowable.

Production of Exothermic Body

Exothermic bodies having a configuration similar to that of the exothermic body 2 shown in FIG. 1(c) were prepared through lab-scale reproduction of the assumed processing using the production apparatus 100 shown in FIG. 3 as the production apparatus. As the base material sheet 21, a 5 cm×5 cm paper made of wood pulp fibers with a basis weight of 32 g/m$^2$ was used. A coated member was formed by uniformly coating one face of the paper with the exothermic composition, and sodium chloride was uniformly sprayed as the halide salt onto the entire upper face of the coated member 4. Next, a layered member was formed by overlaying a 5 cm×5 cm super absorbent sheet with a basis weight of 120 g/m$^2$, as the second base material sheet 22, on the upper face of the coated member 4. The layered member containing the coated member 4 was set to an absolutely dried state by removing water from the layered member through heating in a nitrogen atmosphere at 80° C. for 2 hours and then 62 parts by mass of water was added to 100 parts by mass of the iron powder for an exothermic composition, from the super absorbent sheet side, and thus an exothermic body was produced. The content of the sodium chloride sprayed onto the coated member 4 was set to 10 parts by mass with respect to 100 parts by mass of the iron powder for an exothermic composition. The amount of moisture in the produced exothermic body was 62 parts by mass with respect to 100 parts by mass of the iron powder for an exothermic composition. The basis weight of the exothermic composition in the produced exothermic body was 600 g/m².

Example B2

An exothermic body was produced as in Example B1, except that, in the <Production of Exothermic Body>, after the coated member was set to a wet state by removing water from the coated member through drying in a nitrogen atmosphere at 20° C. for 20 minutes, water was not added. The amount of moisture in the produced exothermic body was 62 parts by mass with respect to 100 parts by mass of the iron powder for an exothermic composition. The basis weight of the exothermic composition in the produced exothermic body was 600 g/m².

Example B3

In the <Production of Exothermic Body>, after a coated member was formed by uniformly coating with the exothermic composition, the coated member was set to a wet state by removing water from the coated member through water absorption through contact with absorbent sponge (Bell Clean D-3 manufactured by Aion Co., Ltd.) made of polyvinyl alcohol, which is an absorbent material at a pressing pressure of 7800 N/m², instead of removal of water through drying. Next, sodium chloride was uniformly sprayed onto the entire upper face of the coated member, and a super absorbent sheet was overlaid on the upper face of the coated member. An exothermic body was produced as in Example B1, except for the above-described aspects. The amount of moisture in the produced exothermic body was 68 parts by mass with respect to 100 parts by mass of the iron powder for an exothermic composition. The basis weight of the exothermic composition in the produced exothermic body was 620 g/m².

Example B4

An exothermic composition for Example B4 was prepared as in Example B1, except that, in Preparation of Exothermic Composition, an iron powder for an exothermic composition, with a bulk density of 0.4 g/cm³, an average particle size of 98 µm, a BET specific surface area of 26 m²/g, and a pore volume as measured using the mercury intrusion method, in a range of 1 µm or more, of 1.3 cm³/g was used, and 154 parts by mass of water was added to 100 parts by mass of the iron powder for an exothermic composition. Then, an exothermic body was produced as in Example B1, except that, in the <Production of Exothermic Body>, the exothermic composition for Example B4 was used, and the coated member was set to an absolutely dried state by removing water from the coated member, and then 110 parts by mass of water was added. The amount of moisture in the produced exothermic body was 110 parts by mass with respect to 100 parts by mass of the iron powder for an exothermic composition. The basis weight of the exothermic composition in the produced exothermic body was 770 g/m².

Example B5

An exothermic composition for Example B5 was prepared as in Example B1, except that, in Preparation of Exothermic Composition, an iron powder for an exothermic composition, with a bulk density of 1.5 g/cm³, an average particle size of 15 µm, a BET specific surface area of 48 m²/g, and a pore volume as measured using the mercury intrusion method, in a range of 1 µm or more, of 0.3 cm³/g was used, and 72 parts by mass of water was added to 100 parts by mass of the iron powder for an exothermic composition. Then, an exothermic body was produced as in Example B1, except that, in the <Production of Exothermic Body>, the exothermic composition for Example B5 was used, and the coated member was set to an absolutely dried state by removing water from the coated member, and then 110 parts by mass of water was added. The amount of moisture in the produced exothermic body was 110 parts by mass with respect to 100 parts by mass of the iron powder for an exothermic composition. The basis weight of the exothermic composition in the produced exothermic body was 770 g/m².

Example B6

An exothermic body was produced as in Example B1, except that, in the <Production of Exothermic Body>, the heating conditions of the layered member for removing water from the coated member were set to heating in a nitrogen atmosphere at 200° C. for 1 hour. The amount of moisture in the produced exothermic body was 62 parts by mass with respect to 100 parts by mass of the iron powder for an exothermic composition. The basis weight of the exothermic composition in the produced exothermic body was 600 g/m².

Example B7

An exothermic body was produced as in Example B3, except that pulp paper (Kaydry 132-S manufactured by Nippon Paper Crecia Co., Ltd.) was used as the absorbent material used to remove water from the coated member, and water was removed through water absorption through contact between the pulp paper and the coated member at a pressing pressure of 11800 N/m². The amount of moisture in the produced exothermic body was 71 parts by mass with respect to 100 parts by mass of the iron powder for an exothermic composition. The basis weight of the exothermic composition in the produced exothermic body was 630 g/m².

Comparative Example B1

An exothermic body was produced as in Example B1, except that, in production of an exothermic body, removal of water and addition of water were not performed. The amount of moisture in the produced exothermic body was 114 parts by mass with respect to 100 parts by mass of the iron powder for an exothermic composition. The basis weight of the exothermic composition in the produced exothermic body was 780 g/m².

Comparative Example B2

An exothermic composition prepared by, in exothermic composition preparation, further mixing 62 parts by mass of water with a mixture of an iron powder for an exothermic composition and a carbon material (activated carbon) was in the form of a granule that was not flowable. The exothermic composition of this comparative example was not flowable, and thus it was not possible to coat the exothermic composition with the base material sheet, and it was not possible to produce an exothermic body.

Comparative Example B3

An exothermic body was produced as in Example B1, except that, in production of an exothermic body, after the coated member was set to a wet state by removing water from the coated member through drying in a nitrogen atmosphere at 20° C. for 1 hour, water was not added. The amount of moisture in the produced exothermic body was 20 parts by mass with respect to 100 parts by mass of the iron powder for an exothermic composition. The basis weight of the exothermic composition in the produced exothermic body was 452 g/m².

Evaluation of Coating Properties

The coating ability when a base material sheet was coated with the exothermic compositions prepared in the above-described examples and comparative examples was evaluated according to the following criteria. Table 2 below shows the results.

A: A base material sheet can be uniformly coated with the exothermic composition.

B: A base material sheet cannot be coated with the exothermic composition.

Evaluation of Exothermic Properties

The exothermic bodies produced in the above-described examples and comparative examples were each enclosed inside a package member in which one face thereof was constituted by a 6.3 cm×6.3 cm air-permeable sheet with an air permeability of 3500 sec/100 mL and the other face was constituted by a 6.3 cm×6.3 cm air-impermeable sheet such that the air-permeable sheet and the super absorbent sheet of the exothermic bodies were in contact with each other, and thus exothermic warmers accommodating the exothermic bodies produced in the above-described examples and comparative examples were produced. The package member was produced by sealing the peripheries of the air-permeable sheet and the air-impermeable sheet. The exothermic properties of the obtained exothermic warmers were evaluated according to the method as defined by JIS S 4100:2007. Specifically, each exothermic warmer of the above-described examples and comparative examples was inserted into a bag made of a needle-punched nonwoven fabric with a basis weight of 100 g/m² and placed on an incubator at 40° C., and the exothermic properties were evaluated. This bag was formed in the shape of a bag by sealing three sides of needle-punched nonwoven fabrics. A thermometer was arranged between the exothermic warmer and the incubator surface such that the air-impermeable sheet of the exothermic warmer faces the thermometer. The exothermic properties were evaluated by plotting changes in the temperature relative to the time and integrating the region with a temperature of over 45° C. with the time, and calculating the area (K·min). The exothermic properties of the exothermic warmers produced using the exothermic bodies of the above-described examples and comparative examples were evaluated according to the following criteria. Table 2 below shows the results.

A: The exothermic properties are at 500 K·min or more.

B: The exothermic properties are at less than 500 K·min.

TABLE 2

| | Example B | | | | | | | Comparative Example B | | |
|---|---|---|---|---|---|---|---|---|---|---|
| | 1 | 2 | 3 | 4 | 5 | 6 | 7 | 1 | 2 | 3 |
| Bulk density of oxidizable metal (g/cm³) | 0.6 | 0.6 | 0.6 | 0.4 | 1.5 | 0.6 | 0.6 | 0.6 | 0.6 | 0.6 |
| Coating of exothermic composition | ○ | ○ | ○ | ○ | ○ | ○ | ○ | ○ | x | ○ |
| Removal of water from coated member | ○ | ○ | ○ | ○ | ○ | ○ | ○ | x | x | ○ |
| Method for removing water | Drying of coated member | Drying of coated member | Water absorption using absorbent material | Drying of coated member | Drying of coated member | Drying of coated member | Water absorption using absorbent material | — | — | Drying of coated member |
| Drying temperature of coated member (° C.) | 80 | 20 | — | 80 | 80 | 200 | — | — | — | 20 |
| Absorbent material used | — | — | Absorbent sponge | — | — | — | Pulp paper | — | — | — |
| Addition of water | ○ | x | x | ○ | ○ | ○ | x | x | x | x |
| Amount of moisture in exothermic composition (with respect to 100 parts by mass of oxidizable metal) | 114 | 114 | 114 | 154 | 72 | 114 | 114 | 114 | 62 | 114 |
| Coating properties | A | A | A | A | A | A | A | A | B | A |
| Amount of moisture in exothermic body (with respect to 100 parts by mass of oxidizable metal) | 62 | 62 | 68 | 110 | 110 | 62 | 71 | 114 | — | 20 |
| Exothermic properties | A | A | A | A | A | A | A | B | — | B |

○: Performed
x: Not performed

As shown in Table 2, the examples each used an iron powder for an exothermic composition (oxidizable metal), with a bulk density in a range of 0.3 to 1.5 g/cm³, and adjusted the amount of moisture in the exothermic composition (the amount of water mixed) to the range of 70 to 160 parts by mass with respect to 100 parts by mass of the iron powder for an exothermic composition, and thus the exothermic compositions were flowable, and had good coating properties. Furthermore, the examples each used an iron powder for an exothermic composition, with a bulk density in a range of 0.3 to 1.5 g/cm³, and adjusted the amount of moisture in the coated member to the range of 30 to 110 parts by mass with respect to 100 parts by mass of the iron powder for an exothermic composition through removal of water, and thus the exothermic properties of the exothermic warmers accommodating the obtained exothermic bodies were good. On the other hand, Comparative Examples B1 and B3 had good coating properties of the exothermic compositions, but the exothermic properties of the exothermic warmers accommodating the exothermic bodies obtained in Comparative Examples B1 and B3 were poor. Furthermore, as described above, according to Comparative Example B2, the exothermic composition was not flowable, and the exothermic body cannot be produced.

Hereinafter, the production method for the iron powder for an exothermic composition according to the third aspect of the invention will be described based on preferred embodiments.

The production method for the iron powder for an exothermic composition according to the third aspect of the invention, that is, the production method for the iron powder for an exothermic composition, with a bulk density of 0.3 to 1.5 g/cm³ (the iron powder for an exothermic composition according to the first aspect of the invention) includes: a reducing step of introducing iron oxide ($Fe_2O_3$) that is a raw material and a solid reductant into a heating furnace, setting the internal portion of the heating furnace to a reducing gas atmosphere through heating under a predetermined condition, thereby reducing the iron oxide to obtain reduced iron (so-called sponge iron); and a milling step of milling the reduced iron. The iron powder for an exothermic composition produced through the production method according to the third aspect of the invention is characterized not only by various physical properties but also an external appearance thereof as shown in FIG. 2(a), and, as described above, the surface layer is constituted by a large number of fibrous matters that are arranged at random in three dimensions.

In the third aspect of the invention, it is preferable to use iron oxide containing iron oxide (III) as a raw material of reduced iron. Typically, as iron oxide that is a raw material of reduced iron, in addition to iron ore, iron oxide (so-called mill scale) produced on a steel material surface during hot-working of steel materials such as steel plates, steel pipes, or section steels, or an iron oxide powder (so-called spray-roasted powder) obtained by spray-drying a pickling waste liquid in pickling line in an iron and steel producing step, and the like may be used, but iron ore (iron ore particles) or a spray-roasted powder is preferable as an iron source in the third aspect of the invention. If a raw material in the form of a fine powder with a low iron oxide (III) purity such as mill scale is used as an iron source, it is difficult to stably produce an iron powder for an exothermic composition having the above-described fibrous structure (see FIG. 2(a)), and desired exothermic properties may not be obtained.

The iron ore (iron oxide) used in the third aspect of the invention is in the form of particles, that is, iron ore particles.

If iron ore (iron ore particles) is used as an iron source, from the viewpoint of the operability of iron ore particles in the reducing step, the average particle size is preferably 0._5 mm or more, and more preferably 1.0 mm or more. If the lower limit of the average particle size of the iron ore particles is within this range, in particular, in a case in which a rotary furnace is used as the heating furnace in the reducing step, dispersion of the iron ore particles in the rotary furnace can be suppressed, and thus a decrease in heat transfer from a heat face of the rotary furnace to the iron ore particles that are to be heated, due to heating of the dispersed iron ore particles through heat transfer from the heat face can be suppressed. Furthermore, in particular, in a case in which a fixed furnace is used as the heating furnace in the reducing step, iron ore particles and a solid reductant can be easily mixed, and, furthermore, when performing the reducing step by filling iron ore particles together with a solid reductant into a heat resistant container (sagger), the efficiency in filling into the heat resistant container can be also improved.

In a case in which a spray-roasted powder (iron oxide) is used as an iron source, from the viewpoint of the operability in the reducing step, the average particle size is preferably 0.01 mm or more, and more preferably 0.02 mm. If the lower limit of the average particle size of the spray-roasted powder is within this range, in particular, in a case in which a rotary furnace is used as the heating furnace in the reducing step, dispersion of the spray-roasted powder in the rotary furnace can be suppressed, and thus leakage of the dispersed spray-roasted powder to the outside of the system can be suppressed. Furthermore, in particular, in a case in which a fixed furnace is used as the heating furnace in the reducing step, a spray-roasted powder and a solid reductant can be easily mixed, and, furthermore, when performing the reducing step by filling a spray-roasted powder together with a solid reductant into a heat resistant container (sagger), the efficiency in filling into the heat resistant container can be also improved.

Furthermore, from the viewpoint of the reducibility of iron oxide in the reducing step and facilitating formation of the above-described fibrous structure, the average particle size of the iron oxide (the iron ore or the spray-roasted powder) is preferably 30 mm or less, and more preferably 25 mm or less. The reductive reaction of the iron oxide in the reducing step progresses from the outer side of the particles toward the inner side, and thus, if the upper limit of the average particle size is within this range, the reductive reaction is likely to progress, and satisfactory reducibility and satisfactory formation of the fibrous structure can be achieved.

In the third aspect of the invention, "average particle size" is 1) a volume-based median diameter as measured using a laser diffraction particle size distribution analyzer, or 2) an arithmetic mean value of measured values obtained by directly measuring a size of objects (iron ore particles) that are to be measured. The volume-based median diameter of 1) can be measured, for example, according to a common method using an LA-950V2 manufactured by Horiba, Ltd. with a standard wet circulation cell settings in which the refractive index is 3.5 for the real part and 3.8i for the imaginary part, water is used as a dispersion medium and the refractive index thereof is 1.33, the circulation speed is 15, and the agitation is 5. Meanwhile, the arithmetic mean value of measured values obtained through direct measurement of 2) is an arithmetic mean value of values obtained by measuring the lengths of long sides and short sides of particles that are to be measured using a measuring device such as a caliper or a micrometer, and, more specifically calculated as an arithmetic mean value of values obtained by measuring the maximum Feret diameters and the minimum Feret diameters of 20 or more particles as defined by JIS-Z8827-1.

The purity of the iron oxide (the iron ore particles or the spray-roasted powder) used in the third aspect of the invention, that is, the mass content of iron oxide (III) in the iron oxide is preferably 90% by mass or more, and more preferably 95% by mass or more, from the viewpoint of reduction in the reducing step. If the purity of the iron oxide is within this range, an iron powder for an exothermic composition having the above-described fibrous structure can be stably produced, and the metal iron content can be increased to a desired range. In order to increase the purity of the iron oxide, it is necessary to repeatedly perform washing with sulfuric acid, but, if the purity of the iron oxide is within this range, the content of sulfur remaining during washing with sulfuric acid can be reduced to a desired range.

There is no particular limitation on the upper limit of the purity of the iron oxide, but, in particular, in a case in which a spray-roasted powder is used as the iron oxide, from the viewpoint of sulfur content, the mass content of iron oxide (III) in the spray-roasted powder as the iron oxide is preferably 99.9% by mass or less, and more preferably 99.6% by mass or less.

Furthermore, in the third aspect of the invention, a solid reductant is used as the reductant that is used together with the iron oxide. Examples of the solid reductant include a carbon-based solid reductant, plastic, wood, and the like, which may be used alone or in combination of two or more.

If a carbon-based solid reductant is used as the solid reductant, examples thereof include coal, coal char, coke; and biomass charcoal such as sawdust coal, coconut shell carbon, and woody charcoal, which may be used alone or in combination of two or more. From the viewpoint of more stably producing an iron powder for an exothermic composition having the above-described fibrous structure (See FIG. 2(a)), biomass charcoal is preferable as the carbon-based solid reductant.

If plastic is used as the solid reductant, examples thereof include high-molecular polymers such as: polyolefin such as polyethylene and polypropylene; polyesters such as polyethylene terephthalate (PET); polybutylene terephtalate (PBT); and polylactic acid, which may be used alone or in combination of two or more. Furthermore, the plastic as the solid reductant may contain inorganic fillers such as talc, silica, calcium carbonate, titanium oxide, or aluminum hydroxide.

If wood is used as the solid reductant, examples thereof include wooden logs, wooden board, sawdust, pulp, wood pellets, and the like, which may be used alone or in combination of two or more. From the viewpoint of raw material handleability in the reducing step, wood pellets are preferable as wood as the solid reductant.

The carbon-based solid reductant used in the third aspect of the invention is preferably in the form of a powder, and, from the viewpoint of the operability of the carbon-based solid reductant in the reducing step, the average particle size thereof is preferably 0.03 mm or more, and more preferably 0.05 mm. If the lower limit of the average particle size of the carbon-based solid reductant is within this range, in particular, in a case in which a rotary furnace is used as the heating furnace in the reducing step, dispersion of the carbon-based solid reductant in the rotary furnace can be suppressed, and thus a decrease in heat transfer from a heat face of the rotary furnace to the carbon-based solid reductant that is to be heated, due to heating of the dispersed carbon-based solid reductant through heat transfer from the heat face can be suppressed. Furthermore, in particular, in a case in which a fixed furnace is used as the heating furnace in the reducing step, a solid reductant and iron ore particles can be easily mixed, and, furthermore, when performing the reducing step by filling a solid reductant and iron oxide (iron ore and a spray-roasted powder) together with a heat resistant container (sagger), the efficiency in filling into the heat resistant container can be also improved.

Furthermore, from the viewpoint of reduction of iron oxide in the reducing step, average particle size of the solid reductant (carbon-based solid reductant, plastic, wood) is preferably 100 mm or less, and more preferably 80 mm or less. If the upper limit of the average particle size of the solid reductant is within this range, formation of the above-described fibrous structure in the reducing step can be achieved. The solid reductant can be formed in the shape of a powder using a method such as compression molding.

Furthermore, if a carbon-based solid reductant is used as the solid reductant, the carbon content of the carbon-based solid reductant is preferably 50% by mass or more, and more preferably 60% by mass or more, with respect to the total mass of the solid reductant. If the carbon content of the carbon-based solid reductant is too low, reduction of the iron oxide (the iron ore or the spray-roasted powder) may be insufficient. The upper limit of the carbon content of the carbon-based solid reductant is preferably 95% by mass or less, and more preferably 90% by mass or less, from the viewpoint of the relationship with the later-described volatile matter. The carbon content of the carbon-based solid reductant is measured according to the method for measuring the fixed carbon content in coal and coke as defined by JIS M8812.

Furthermore, the volatile matter content of the solid reductant (the carbon-based solid reductant, the plastic, and the wood) used in the third aspect of the invention is 10% by mass or more, and preferably 15% by mass or more, with respect to the total mass of the solid reductant. The volatile matter content is a total content of matters that vaporize from the solid reductant when the solid reductant is heated. If the lower limit of the volatile matter content of the solid reductant is within this range, reduction of the iron oxide (the iron ore or the spray-roasted powder) can be sufficiently performed.

Furthermore, if a carbon-based solid reductant is used as the solid reductant, the upper limit of the volatile matter content of the carbon-based solid reductant is preferably 50% by mass or less, and more preferably 40% by mass or less, from the viewpoint of the relationship with the above-described carbon content. The volatile matter content of the solid reductant is measured according to the method for determining the volatile matter in coal and coke as defined by JIS M8812.

Furthermore, the sulfur content of the solid reductant (the carbon-based solid reductant, the plastic, or the wood) used in the third aspect of the invention is preferably 500 ppm or less, more preferably 400 ppm or less, and ideally zero, with respect to the total mass of the solid reductant. If the solid reductant contains sulfur, sulfur gas derived from the solid reductant may be produced inside a heating furnace in the reducing step, and corrode production facilities such as the heating furnace. In regards to this aspect, if the sulfur content in the solid reductant is 500 ppm or less, the atmosphere of the internal portion of the heating furnace contains almost no sulfur gas, and thus production facilities such as the heating furnace are unlikely to be corroded.

In the reducing step, the iron oxide (the iron ore or the spray-roasted powder) and the solid reductant (the carbon-based solid reductant, the plastic, or the wood) are heated. As the method of the heating, methods commonly used to produce sponge iron may be used as appropriate, and, typically, a method is used in which iron oxide and a solid reductant are filled into a heat resistant container called sagger, and are indirectly heated via the heat resistant container in a heating furnace.

It is preferable that, in the reducing step, the iron oxide (the iron ore or the spray-roasted powder) and the solid reductant (the carbon-based solid reductant, the plastic, or the wood) each in a powder state are mixed, and the mixture is heated, in view of uniformity in forming the above-described fibrous structure. Specifically, for example, a method is used in which a mixture obtained by mixing the iron oxide and the solid reductant each in a powder state is filled into a hollow portion of a heat resistant container (sagger) in the shape of a hollow cylinder, and is indirectly heated via the heat resistant container in a heating furnace. The content mass ratio between the iron oxide and the solid reductant in the mixture is, as iron oxide/solid reductant, preferably 1 or more, and more preferably 1.5 or more, and is preferably 18 or less, and more preferably 9 or less.

The reducing step is performed using a heating furnace. As the heating furnace, heating furnaces commonly used to produce sponge iron may be used with no particular limitation, and either a rotary furnace or a fixed furnace or a non-rotational type may be used. Furthermore, the heating furnace may be either of an internal combustion type in which a raw material (iron oxide and a solid reductant) and a heating medium such as fuel gas are brought into direct contact with each other, that is, a raw material is directly heated, or of an external combustion type in which a raw material and a heating medium are not brought into direct contact with each other, and a furnace wall defining the internal portion of a heating furnace to which a raw material has been introduced is heated from the outside using a heating medium, that is, a raw material is indirectly heated through heat transfer via the furnace wall. Specific examples of the rotary furnace include rotary kilns of the internal combustion type and the external combustion type. Rotary kilns of the internal combustion type may be, for example, either of a type in which fuel gas sent into the heating furnace is combusted, and a raw material is heated with heat of the combustion, or of a type in which a raw material is heated with hot gas blown into the heating furnace. Typically, in the case of a heating furnace of the internal combustion type, a raw material is in direct contact with a heating medium such as combustion gas or hot gas, and thus powder dust or the like contained in the heating medium may be mixed in the raw material, and lower the quality of products. On the other hand, in the case of a heating furnace of the external combustion type, a raw material is not in contact with a heating medium, and thus its thermal efficiency is lower than that of the internal combustion type, but the quality does not decrease due to powder dust or the like mixed. From the viewpoint of more stably producing an iron powder for an exothermic composition having the above-described fibrous structure (See FIG. 2(a)), it is preferable to perform heating using a fixed furnace or rotary furnace of the external combustion type.

The atmosphere of the internal portion of the heating furnace to which a raw material (iron oxide and a solid reductant) is introduced has to be an air or inert gas atmosphere containing no sulfur gas. If there is sulfur gas inside the heating furnace, production facilities such as the heating furnace may corrode. The phrase "containing no sulfur gas" means a state in which, specifically, the sulfur gas concentration inside the heating furnace is preferably 500 ppm or less, and more preferably 100 ppm or less, with respect to the total volume inside the furnace. Accordingly, in the third aspect of the invention, it is preferable that sulfur gas is not introduced to the inside of the heating furnace, and a material with a sulfur content that is as low as possible is used as the raw material.

In the reducing step, reduced iron (sponge iron) is obtained by introducing a raw material (iron oxide and a solid reductant) into a heating furnace whose internal portion contains no sulfur gas or is set to an air or inert gas atmosphere, and setting the internal portion to a reducing gas atmosphere through heating under a condition that an ambient temperature of the internal portion is from 900 to 1000° C., thereby reducing the iron oxide. The atmosphere of the internal portion of the heating furnace is an atmosphere with air or inert gas such as nitrogen when heating is started. However, in accordance with an increase in the temperature of the raw material, the solid reductant (the carbon-based solid reductant, the plastic, or the wood) decomposes, and carbon monoxide is produced and diffused inside the heating furnace, and thus the atmosphere of the internal portion changes to a reducing gas atmosphere. The phrase "reducing gas atmosphere" is an atmosphere containing carbon monoxide, hydrogen, hydrocarbon gas (methane, ethane, propane, etc.), or the like. In the reducing gas atmosphere, carbon monoxide reduces iron oxide (the iron ore or the spray-roasted powder) to produce reduced iron (Fe). At this time, carbon dioxide is simultaneously produced, but the carbon dioxide reacts with the solid reductant to form carbon monoxide, and the carbon monoxide is diffused inside the heating furnace and reduces iron oxide.

In the heating in the reducing step, if the ambient temperature of the internal portion of the heating furnace is outside the range of 900 to 1000° C., it is difficult to produce an iron powder for an exothermic composition having the above-described fibrous structure (See FIG. 2(a)). The ambient temperature of the internal portion of the heating furnace during the heating is preferably 910° C. or more, and more preferably 920° C. or more, and is preferably 995° C. or less, and more preferably 990° C. or less.

Furthermore, the heating time in the reducing step (the period of time during which the ambient temperature is kept at 900 to 1000° C.) is preferably 0.5 hours or more, and more preferably 1 hour or more, and is preferably 8 hours or less, and more preferably 6 hours or less.

In the heating in the reducing step, from the viewpoint of facilitating the reductive reaction of the iron oxide, a larger total content of carbon monoxide and carbon dioxide in the reducing gas atmosphere is more preferable, and the total content is preferably 50% by volume or more, and more preferably 60% by volume. The total content of carbon monoxide and carbon dioxide in the reducing gas atmosphere can be adjusted by adjusting the amount of solid reductant used, purge gas, and the like as appropriate.

In the reducing step, it is preferable that oxygen in an amount corresponding to 1.5% by mass or less of the iron oxide in the internal portion of the heating furnace is introduced to the internal portion during heating. The reductive reaction of the iron oxide is an endothermic reaction. In particular, in a case in which a reducing furnace that is used is large, a difference between the temperatures inside and outside the heating furnace appears in accordance with progress of the reductive reaction, and thus there may be a concern that iron oxide introduced into the heating furnace is not sufficiently reduced. On the other hand, if oxygen is introduced to the heating furnace, carbon in the solid reductant is combusted with the introduced oxygen to generate combustion heat. Thus, the amount of heat that has been lost through the reductive reaction is compensated for by this heat of the combustion, and thus such a concern is eliminated. If the amount of oxygen introduced to the heating furnace is set to an amount that is not too small and that is within the above-described range, the amount of heat inside the heating furnace can be compensated for, and iron oxide can be sufficiently reduced. Furthermore, if the amount of oxygen introduced to the heating furnace is set to an amount that is not too small and that is within the above-described range, the reduced iron oxide can be prevented from oxidizing again. Note that a criterion for the amount of oxygen introduced is an iron oxide content in an iron source (the iron ore or the spray-roasted powder) introduced to the heating furnace.

The reduced iron obtained through the reducing step is subjected to mineral processing as necessary, and is then milled (milling step). The mineral processing is processing for selecting reduced iron with a high metal iron purity, and known methods may be used with no particular limitation. Examples of the methods include a method in which metal iron that is magnetic and non-magnetic components (gangue) are separated using a magnetic force (magnetic dressing method).

There is no particular limitation on the method for milling the reduced iron in the milling step, and known methods may be used, examples of which includes those performed using known mills such as a rod mill, a roller crusher, and a ball mill.

It will be appreciated that, from the viewpoint of more stably producing an iron powder for an exothermic composition having the above-described fibrous structure (See FIG. 2(a)), it is preferable that the milling into a powder form is performed such that the fibrous structure of reduced iron immediately after reduction is maintained to the extent possible, and, in order to realize this aspect, it is preferable that the milling level of the reduced iron is lower than that in conventional techniques. For example, in a conventional step of milling reduced iron, generally, milling is performed on 1.0 kg of reduced iron for approximately 8 to 12 minutes using a vibration rod mill (e.g., product name "MB-1" manufactured by Chuo Kakohki Co., Ltd.), whereas, in the preferable production of an iron powder for an exothermic composition according to the third aspect of the invention, milling is performed on 0.1 kg of reduced iron for approximately 5 to 30 seconds at a number of rotations of 700 to 1000 rpm using a vibratory disc mill (e.g., product name "RS200" manufactured by Verder Scientific Co., Ltd.). When such a relatively low level of milling is performed on reduced iron, it is possible to more stably obtain an iron powder with a bulk density in a range of 0.3 to 1.5 g/cm$^3$ and having the above-described fibrous structure.

The iron powder obtained through the milling step is sieved as necessary into particles with a desired particle size and is further heated, so that an iron powder for an exothermic composition is obtained.

The iron powder for an exothermic composition produced through the production method according to the foregoing third aspect of the invention is used as a material for an exothermic composition, as the iron powder for an exothermic composition according to the first aspect of the invention. The description in the first aspect of the invention is applied to a specific use mode of the iron powder for an exothermic composition produced through the production method according to the foregoing third aspect of the invention. FIG. 1 shows the exothermic warmer 1, which is an embodiment of an exothermic warmer using the iron powder for an exothermic composition produced through the production method according to the foregoing third aspect of the invention. The exothermic warmer 1 is as described above, and the description in the first aspect of the invention is applied unless otherwise described.

The average particle size of the iron powder for an exothermic composition produced through the production method according to the foregoing third aspect of the invention is preferably 30 μm or more, and more preferably 40 μm or more, and is preferably 150 μm or less, and more preferably 100 μm or less. If the average particle size of the iron powder for an exothermic composition is within this range, the above-described effects (the effects of improving the exothermic properties and the handleability of an exothermic composition or an exothermic body) can be more reliably achieved. The average particle size of the iron powder for an exothermic composition can be adjusted by adjusting the milling level in the above-described milling step as appropriate.

The metal iron content of the iron powder for an exothermic composition produced through the production method according to the foregoing third aspect of the invention is preferably 60% by mass or more, and more preferably 70% by mass or more, and is preferably 95% by mass or less, and more preferably 90% by mass or less. If the metal iron content in the iron powder for an exothermic composition is within this range, the above-described effects (the effects of improving the exothermic properties and the handleability of an exothermic composition or an exothermic body) can be more reliably achieved. The metal iron content in the iron powder is measured, for example, using the bromine-methanol titrimetric method as defined by ISO5416, or the like. The metal iron content in the iron powder can be adjusted by adjusting the reducing conditions, the heating conditions after reduction, and the like as appropriate.

The third aspect of the invention was described above based on an embodiment thereof, but the third aspect of the invention is not limited to the foregoing embodiment, and may be changed as appropriate. Regarding the foregoing embodiment of the third aspect of the invention, the following notes are further disclosed.

<C1>

A production method for the iron powder for an exothermic composition as set forth in clause <A1> (an iron powder for an exothermic composition, with a bulk density of 0.3 to 1.5 g/cm$^3$), comprising the steps of:

a reducing step of introducing iron oxide and a solid reductant with a volatile matter content of 10% by mass or more into a heating furnace whose internal portion contains no sulfur gas or is set to an air or inert gas atmosphere, and setting the internal portion to a reducing gas atmosphere through heating under a condition that an ambient temperature of the internal portion is from 900 to 1000° C., thereby reducing the iron oxide to obtain reduced iron; and a step of milling the reduced iron.

<C2>

The production method for the iron powder for an exothermic composition as set forth in clause <C1>, wherein the iron oxide and the solid reductant each in a powder state are mixed, and the mixture is heated in the reducing step.

<C3>

The production method for the iron powder for an exothermic composition as set forth in clause <C1> or <C2>, wherein the solid reductant is a carbon-based solid reductant, and an average particle size of the carbon-based solid reductant is from 0.03 to 100 mm, a carbon content thereof is 50% by mass or more, and a sulfur content thereof is 500 ppm or less.

<C4>

The production method for the iron powder for an exothermic composition, as set forth in clause <C3>, wherein the average particle size of the carbon-based solid reductant is preferably 0.03 mm or more, and more preferably 0.05 mm or more, and is preferably 100 mm or less, and more preferably 80 mm or less.

<C5>

The production method for the iron powder for an exothermic composition as set forth in any one of clauses <C1> to <C4>, wherein the solid reductant is a carbon-based solid reductant, and a carbon content of the carbon-based solid reductant is preferably 50% by mass or more, and more preferably 60% by mass or more, and is preferably 95% by mass or less, and more preferably 90% by mass or less, with respect to a total mass of the solid reductant.

<C6>

The production method for the iron powder for an exothermic composition as set forth in any one of clauses <C1> to <C5>, wherein the solid reductant is a carbon-based solid reductant, and a sulfur content of the carbon-based solid reductant is preferably 500 ppm or less, and more preferably 400 ppm or less, with respect to a total mass of the solid reductant.

<C7>

The production method for the iron powder for an exothermic composition as set forth in clause <C1> or <C2>, wherein the solid reductant is plastic.

<C8>

The production method for the iron powder for an exothermic composition as set forth in clause <C1> or <C2>, wherein the solid reductant is wood.

<C9>

The production method for the iron powder for an exothermic composition as set forth in any one of clauses <C1> to <C8>, wherein the iron oxide is iron ore, and an average particle size of the iron ore is preferably 0.5 mm or more, and more preferably 1.0 mm or more, and is preferably 30 mm or less, and more preferably 25 mm or less, and, specifically, it is preferably from 0.5 to 30 mm, and more preferably from 1.0 to 25 mm.

<C10>

The production method for the iron powder for an exothermic composition as set forth in any one of clauses <C1> to <C8>, wherein the iron oxide is a spray-roasted powder, and an average particle size of the spray-roasted powder is preferably 0.01 mm or more, and more preferably 0.02 mm or more, and is preferably 30 mm or less, and more preferably 25 mm or less, and, specifically, it is preferably from 0.01 to 30 mm, and more preferably from 0.02 to 25 mm.

<C11>

The production method for the iron powder for an exothermic composition as set forth in any one of clauses <C1> to <C10>, wherein, in the reducing step, oxygen in an amount corresponding to 1.5% by mass or less of the iron oxide in the internal portion of the heating furnace is introduced to the internal portion.

<C12>

The production method for the iron powder for an exothermic composition as set forth in any one of clauses <C1> to <C11>, wherein a total content of carbon monoxide and carbon dioxide in the reducing gas atmosphere is preferably 50% by volume or more, and more preferably 60% by volume or more.

<C13>

The production method for the iron powder for an exothermic composition as set forth in any one of clauses <C1> to <C12>, wherein the heating furnace is a fixed furnace or rotary furnace of the external combustion type in which a material that is to be heated is heated through heat transfer via a furnace wall.

<C14>

The production method for the iron powder for an exothermic composition as set forth in any one of clauses <C1> to <C13>, wherein the metal iron content in the iron powder for an exothermic composition is preferably 60% by mass or more, and more preferably 70% by mass or more, and is preferably 95% by mass or less, and more preferably 90% by mass or less, and, specifically, it is preferably from 60 to 95% by mass, and more preferably from 70 to 90% by mass.

<C15>

The production method for the iron powder for an exothermic composition as set forth in any one of clauses <C1> to <C14>, wherein the ambient temperature of the internal portion of the heating furnace during the heating is preferably 910° C. or more, and more preferably 920° C. or more, and is preferably 995° C. or less, and more preferably 990° C. or less.

<C16>

The production method for the iron powder for an exothermic composition as set forth in any one of clauses <C1> to <C15>, wherein a heating time in the reducing step, that is, a period of time during which the ambient temperature is kept at 900 to 1000° C. is preferably 0.5 hours or more, and more preferably 1 hour or more, and is preferably 8 hours or less, and more preferably 6 hours or less.

<C17>

The production method for the iron powder for an exothermic composition as set forth in any one of clauses <C1> to <C16>, wherein, in the step of milling the reduced iron, milling is performed on 0.1 kg of reduced iron for approximately 5 to 30 seconds at a number of rotations of 700 to 1000 rpm using a vibratory disc mill.

EXAMPLES

Hereinafter, the third aspect of the invention will be more specifically described by way of examples, but the third aspect of the invention is not limited to these examples.

Examples C1 to C4, and C7 to C10 and Comparative Examples C1 to C6

Iron ore (containing $Fe_2O_3$: 96.4% by mass, $SiO_2$: 2.0% by mass, and $Al_2O_3$: 1.6% by mass, and having an average particle size of 20 mm) was used as an iron source. A mixed powder was obtained by placing 70 g of iron source and 30 g of solid reductant in a polyethylene bag (Unipack F-8 manufactured by Seisannipponsha Ltd.) and shaking the bag, and the mixed powder was filled into a heat resistant container made of SUS303 with an inner diameter of 100 mm and a length of 110 mm. A fixed furnace of the external combustion type (KDF-900GL manufactured by Denken. Co. ltd.) was used as the heating furnace, the container into which the mixture had been filled was allowed to stand inside the heating furnace, the container was heated, and thus reduction treatment of the iron source was performed to obtain reduced iron (reducing step). The heating (reduction treatment) was performed in a nitrogen atmosphere by increasing the temperature from room temperature at 10° C./min to a predetermined temperature, keeping the temperature at the predetermined temperature for 2.5 hours, and then slowly cooling the resultant substance to room temperature. Furthermore, oxygen in a predetermined amount was introduced into the heating furnace during the heating. After heating, the reduced iron was taken out from the container, and milled at a number of rotations of 700 rpm for 10 seconds using a vibratory disc mill (RS200 (standard mill set made of SUS) manufactured by Verder Scientific Co., Ltd.) to obtain a coarse iron powder (milling step). A coarse powder was removed from the obtained coarse iron powder through sieving for 5 minutes using a rotating and tapping test apparatus (1038-A manufactured by Yoshida Manufacturing Co., Ltd.) with a test sieve (JTS-250-60-37 manufactured by Tokyo Screen Co., Ltd.) with a sieve opening size of 250 μm, to obtain a target iron powder for an exothermic composition. All the solid reductants that were used were carbon-based solid reductants, and details thereof are as follows.

- Solid reductant A: Coconut shell carbon (with an average particle size of 0.05 mm, a carbon content of 78% by mass, a volatile matter content of 15% by mass, and a sulfur content of 300 ppm)
- Solid reductant B: Sawdust coal (with an average particle size of 0.15 mm, a carbon content of 77% by mass, a volatile matter content of 21% by mass, and a sulfur content of 50 ppm)
- Solid reductant C: Woody charcoal (with an average particle size of 0.2 mm, a carbon content of 74% by mass, a volatile matter content of 25% by mass, and a sulfur content of 40 ppm)
- Solid reductant D: Char (with an average particle size of 20 mm, a carbon content of 85% by mass, a volatile matter content of 9% by mass, and a sulfur content of 2500 ppm)
- Solid reductant E: Coke (with an average particle size of 0.05 mm, a carbon content of 90% by mass, a volatile matter content of 3% by mass, and a sulfur content of 4600 ppm)

Example C5

An iron powder for an exothermic composition was obtained as in Example C1, except that iron ore (containing $Fe_2O_3$: 96.4% by mass, $SiO_2$: 2.0% by mass, and $Al_2O_3$: 1.6% by mass, and having an average particle size of 10 mm) was used as an iron source.

Example C6

An iron powder for an exothermic composition was obtained as in Example C1, except that iron ore (containing $Fe_2O_3$: 96.4% by mass, $SiO_2$: 2.0% by mass, and $Al_2O_3$: 1.6% by mass, and having an average particle size of 0.5 mm) was used as an iron source.

Example C11

An iron powder for an exothermic composition was obtained as in Example C1, except that 13.3 kg of iron source and 5.7 kg of solid reductant B as solid reductant were introduced to a batch-type rotary furnace (with an inner diameter of 300 mm, and a heating zone length of 1000 mm, and made of SUS310S), and heating (reduction treatment) was performed by increasing the temperature with an air flow rate of 1 L/min from room temperature at 10° C./min to a predetermined temperature, keeping the temperature with an air flow rate of 0 L/min at the predetermined temperature for 2.5 hours, and then slowly cooling the resultant substance to room temperature.

Example C12

An iron powder for an exothermic composition was obtained as in Example C1, except that a spray-roasted powder (JC-DS manufactured by JFE Chemical Corporation) was used as an iron source, 60 g of, plastic (solid reductant F: polyethylene (Novatec LD manufactured by Mitsubishi Chemical Corporation, with a volatile matter content of 100% by mass)) was used as a solid reductant, a lidded heat resistant container made of SUS303 with an inner diameter of 100 mm and a length of 110 mm was used, the temperature was increased from room temperature at 25° C./min to a predetermined temperature and kept for 3.5 hours, and oxygen was not introduced to the heating furnace during the heating.

Example C13

An iron powder for an exothermic composition was obtained as in Example C12, except that plastic (solid reductant G: polypropylene (MF650Y manufactured by LyondellBasell, with a volatile matter content of 100% by mass)) was used as a solid reductant.

Example C14

An iron powder for an exothermic composition was obtained as in Example C12, except that 30 g of solid reductant F as a solid reductant and 10 g of solid reductant A were used, and oxygen in a predetermined amount was introduced into the heating furnace during the heating.

Example C15

An iron powder for an exothermic composition was obtained as in Example C12, except that 70 g of iron ore as an iron source 60 g of wood (solid reductant H: wood pellets, Rakutin Neko Toire, deodorant and antimicrobial pine sand, manufactured by Irisohyama Inc., with a volatile matter content of 86% by mass) as a solid reductant were used, and the temperature was kept at the predetermined temperature for 3.5 hours.

Example C16

An iron powder for an exothermic composition was obtained as in Example C14, except that 70 g of iron ore an iron source and 60 g of plastic (solid reductant G) as a solid reductant were used.

Comparative Example C7

An iron powder for an exothermic composition was obtained as in Example C1, except that no solid reductant was used.

Comparative Example C8

An iron powder for an exothermic composition was obtained as in Example C11, except that 13.3 kg of iron source and 5.7 kg of solid reductant D as solid reductant were introduced to a batch-type rotary furnace (with an inner diameter of 300 mm, and a heating zone length of 1000 mm, and made of SUS310S), and heating (reduction treatment) was performed by increasing the temperature with an air flow rate of 1 L/min from room temperature at 10° C./min to a predetermined temperature, keeping the temperature with an air flow rate of 0 L/min at the predetermined temperature for 2.5 hours, and then slowly cooling the resultant substance to room temperature.

Evaluation Test

The bulk densities and the metal iron contents of the iron powders for an exothermic composition obtained in the above-described examples and comparative examples were measured, and evaluation was performed as to whether or not they had a fibrous structure as shown in FIG. 2(a) using an electron microscope. Furthermore, the internal portion of the heating furnace used to produce the iron powders for an exothermic composition was visually observed to perform evaluation as to whether or not the furnace elements had corroded.

Furthermore, coating materials were prepared using the following method using the iron powders for an exothermic composition obtained in the above-described examples and comparative examples, and the preservation stabilities of the coating materials were evaluated using the following method.

Furthermore, exothermic bodies were produced using the following method using the above-described coating materials, and the exothermic properties of the exothermic bodies were evaluated using the following method.

Tables 3 and 4 below show the results.

Preparation of Coating Material

Coating materials were prepared using the iron powders of the above-described examples and comparative examples. The composition of each coating material was set so as to contain 100 parts by mass of iron powder, 8 parts by mass of carbon material (activated carbon), 0.3 parts by mass of thickener (guar gum), 60 parts by mass of water, and 5 parts by mass of electrolyte (sodium chloride). The coating material was prepared by, first, mixing the iron powder and the carbon material, adding a mixed liquid of the water and the thickener to the mixture, and uniformly mixing the resultant substance.

Production of Exothermic Body

Exothermic bodies having a configuration similar to that of the exothermic body 2 shown in FIG. 1(c) were prepared using the coating materials prepared using the iron powders of the above-described examples and comparative examples. A 5 cm×5 cm paper made of wood pulp fibers with a basis weight of 70 g/m² was used as the base material sheet 21, and a 5 cm×5 cm super absorbent sheet described below with a basis weight of 80 g/m² was used as the base material sheet 22. A coat layer was formed by uniformly coating one face of the base material sheet 21 with the coating material, a powder of a halide salt (sodium chloride) was uniformly added to the entire coat layer, and then the base material sheet 22 was overlaid thereon, and thus an exothermic body having a configuration similar to that of the exothermic body 2 was produced. In the exothermic composition, the content of the halide salt was set to 5 parts by mass with respect to 100 parts by mass of the iron powder in the exothermic composition. In the exothermic body, the basis weight of the exothermic composition was 587 g/m².

Preparation of Super Absorbent Sheet

The super absorbent sheet used as the base material sheet 22 was prepared using the method described in the specification of Japanese Patent No. 5894747. This super absorbent sheet is one sheet having a configuration in which particles of a sodium polyacrylate-based superabsorbent polymer were present mainly at substantially the center in the thickness direction of the sheet, and were not substantially present on the surfaces of the sheet. The super absorbent sheet had layers of hydrophilic cross-linked high-volume cellulose fibers on the front and back sides sandwiching the region with superabsorbent polymer particles therebetween. The cross-linked high-volume cellulose fibers had a fiber roughness of 0.22 mg/m and an average fiber length of 2.5 mm. The layers of the cross-linked high-volume cellulose fibers further contained softwood bleached kraft pulp and a paper strength agent (polyvinyl alcohol). The superabsorbent polymer particles that were used had an average particle size of 340 nm. The superabsorbent polymer particles had a basis weight of 30 g/m², and the super absorbent sheet, that is, the base material sheet 22 had a basis weight of 80 g/m².

Method for Evaluating Preservation Stability of Coating Materials

The preservation stability of each coating material was evaluated through comparison between the solid content of the coating material immediately after production and the solid content after the coating material immediately after production was allowed to stand for 24 hours. The solid content of the coating material was evaluated by removing moisture of the coating material through heating and measuring the remaining mass. For example, 1 g of coating material was dried at 120° C. for 30 minutes, and the remaining mass was measured using a moisture analyzer HR83 manufactured by Mettler Toledo. The solid content immediately after production was evaluated such that, if the solid content after being allowed to stand for 24 hours does not change, it was evaluated as Good (highest evaluation), and, if the solid content after 24 hours changes by 2% or more, it was evaluated as NG. The preservation stability of the coating material is closely related to the handleability, and thus a coating material with high preservation stability can be evaluated as being excellent in terms of handleability, and being easy to handle and excellent in terms of coating suitability.

Method for Evaluating Exothermic Properties of Exothermic Bodies

Exothermic warmers having a configuration similar to that of the exothermic warmer 1 shown in FIG. 1 were produced using the exothermic bodies produced in the above-described examples and comparative examples. As a package member that wrapped around each exothermic body, a package member was used in which a cover sheet arranged on one face side of the exothermic body was constituted by a 6.3 cm×6.3 cm air-permeable sheet with an air permeability of 3500 sec/100 mL, and a cover sheet arranged on the other face side of the exothermic body was constituted by a 6.3 cm×6.3 cm air-impermeable sheet. Each exothermic body that is to be evaluated was accommodated inside (between the cover sheets of) the package member such that the air-permeable sheet of the package member and the super absorbent sheet of the exothermic body were in contact with each other, and an exothermic warmer accommodating the exothermic body was produced by sealing the peripheral edges of the cover sheets.

The exothermic properties of the thus produced exothermic warmers using the exothermic bodies of the above-described examples and comparative examples were evaluated according to the method as defined by JIS S 4100:2007. Specifically, each exothermic warmer that is to be evaluated was accommodated in a bag made of a needle-punched nonwoven fabric with a basis weight of 100 g/m², and the bag was directly placed on the upper face of an incubator at 40° C., and the exothermic properties were evaluated. This bag was formed in the shape of a bag by sealing three sides of needle-punched nonwoven fabrics in the shape of rectangles in plane view. A thermometer used to measure the temperature was arranged between the exothermic warmer and the upper face of the incubator, that is, the face on which the exothermic warmer had been placed, such that the base material sheet 21 faces the thermometer. The temperature properties of the exothermic bodies were evaluated by comparing areas (K·min) obtained by plotting changes in the temperature relative to the time and integrating the region with a temperature of over 45° C. with the time, wherein, if the area was over 300 K·min, it was evaluated as Good (highest evaluation), and, if the area was less than or equal to 300 K·min, it was evaluated as NG.

TABLE 3

| | | Example C | | | | | | | |
|---|---|---|---|---|---|---|---|---|---|
| | | 1 | 2 | 3 | 4 | 5 | 6 | 7 | 8 |
| Reducing step | Average particle size of iron ore (mm) | 20 | 20 | 20 | 20 | 10 | 0.5 | 20 | 20 |
| | Type of solid reductant | A | A | A | A | A | A | B | B |
| | Type of heating furnace | External combustion fixed furnace | External combustion fixed furnace | External combustion fixed furnace | External combustion fixed furnace | External combustion fixed furnace | External combustion fixed furnace | External combustion fixed furnace | External combustion fixed furnace |
| | Ambient temperature of internal portion of heating furnace (° C.) | 950 | 920 | 980 | 1000 | 950 | 950 | 950 | 980 |
| | Amount of oxygen introduced during heating (with respect to iron oxide, mass %) | 0.4 | 0.4 | 0.4 | 0.4 | 0.4 | 0.4 | 0.4 | 0.4 |
| | Total content of CO and $CO_2$ in reducing atmosphere (mass %) | 60 | 60 | 60 | 60 | 60 | 60 | 60 | 60 |
| Iron powder evaluation | Bulk density (g/cm³) | 0.5 | 0.7 | 0.4 | 0.4 | 0.5 | 0.3 | 0.6 | 0.6 |
| | Metal iron content (mass %) | 82 | 80 | 85 | 89 | 84 | 84 | 81 | 84 |
| | Presence/absence of fibrous structure | Presence | Presence | Presence | Presence | Presence | Presence | Presence | Presence |
| | Preservation stability of coating material | Good | Good | Good | Good | Good | Good | Good | Good |
| | Exothermic properties of exothermic body | Good | Good | Good | Good | Good | Good | Good | Good |
| Presence/absence of corrosion of furnace elements | | Absence | Absence | Absence | Absence | Absence | Absence | Absence | Absence |

| | | Example C | | | | | | | |
|---|---|---|---|---|---|---|---|---|---|
| | | 9 | 10 | 11 | 12 | 13 | 14 | 15 | 16 |
| Reducing step | Average particle size of iron ore (mm) | 20 | 20 | 20 | — | — | — | 20 | 20 |
| | Type of solid reductant | B | C | B | F | G | F/A | H | G |
| | Type of heating furnace | External combustion fixed furnace | External combustion fixed furnace | External combustion fixed furnace | External combustion fixed furnace | External combustion fixed furnace | External combustion fixed furnace | External combustion fixed furnace | External combustion fixed furnace |
| | Ambient temperature of internal portion of heating furnace (° C.) | 1000 | 980 | 950 | 1000 | 1000 | 1000 | 950 | 1000 |
| | Amount of oxygen introduced during heating (with respect to iron oxide, mass %) | 0.4 | 0.4 | 0.2 | 0.0 | 0.0 | 0.4 | 0.0 | 0.4 |
| | Total content of CO and $CO_2$ in reducing atmosphere (mass %) | 60 | 60 | 75 | 60 | 60 | 60 | 60 | 60 |

TABLE 3-continued

| | | | | | | | | | |
|---|---|---|---|---|---|---|---|---|---|
| Iron powder evaluation | Bulk density (g/cm³) | 0.5 | 0.6 | 0.6 | 0.7 | 0.8 | 0.6 | 0.5 | 0.8 |
| | Metal iron content (mass %) | 86 | 84 | 82 | 74 | 71 | 78 | 83 | 70 |
| | Presence/absence of fibrous structure | Presence | Presence | Presence | Presence | Presence | Presence | Presence | Presence |
| | Preservation stability of coating material | Good | Good | Good | Good | Good | Good | Good | Good |
| | Exothermic properties of exothermic body | Good | Good | Good | Good | Good | Good | Good | Good |
| Presence/absence of corrosion of furnace elements | | Absence | Absence | Absence | Absence | Absence | Absence | Absence | Absence |

Note)
Volatile matter content: Solid reductant A: 15 mass %,
Solid reductant B: 21 mass %,
Solid reductant C: 25 mass %,
Solid reductant F: 100 mass %,
Solid reductant G: 100 mass %,
Solid reductant H: 86 mass %

TABLE 4

| | | Comparative Example C | | | | | | | |
|---|---|---|---|---|---|---|---|---|---|
| | | 1 | 2 | 3 | 4 | 5 | 6 | 7 | 8 |
| Reducing step | Average particle size of iron ore (mm) | 20 | 20 | 20 | 20 | 20 | 20 | 20 | 20 |
| | Type of solid reductant | A | A | D | D | D | E | — | D |
| | Type of heating furnace | External combustion fixed furnace | External combustion fixed furnace | External combustion fixed furnace | External combustion fixed furnace | External combustion fixed furnace | External combustion fixed furnace | External combustion fixed furnace | External combustion fixed rotary furnace |
| | Ambient temperature of internal portion of heating furnace (° C.) | 850 | 1100 | 850 | 950 | 1100 | 950 | 950 | 950 |
| | Amount of oxygen introduced during heating (with respect to iron oxide, mass %) | 0.4 | 0.4 | 0.4 | 0.4 | 0.4 | 0.4 | 0.4 | 0.2 |
| | Total content of CO and $CO_2$ in reducing atmosphere (mass %) | 38 | 60 | 40 | 60 | 60 | 40 | 0 | 58 |
| Iron powder evaluation | Bulk density (g/cm³) | 1.7 | 2.1 | 1.9 | 0.6 | 2.3 | 1.8 | — | 2.0 |
| | Metal iron content (mass %) | 40 | 92 | 45 | 82 | 93 | 30 | 0 | 73 |
| | Presence/absence of fibrous structure | Absence | Absence | Absence | Presence | Absence | Absence | Absence | Absence |
| | Preservation stability of coating material | NG | Good | NG | Good | Good | NG | — | Good |
| | Exothermic properties of exothermic body | NG | NG | NG | Good | NG | NG | — | NG |
| Presence/absence of corrosion of furnace elements | | Absence | Absence | Presence | Presence | Presence | Presence | Absence | Presence |

Note)
Volatile matter content: Solid reductant A: 15 mass %,
Solid reductant D: 9 mass %,
Solid reductant E: 3 mass %

INDUSTRIAL APPLICABILITY

According to the first aspect of the invention, it is possible to provide an iron powder for an exothermic composition, and an exothermic composition that are excellent in terms of exothermic properties and handleability.

According to the second aspect of the invention, it is possible to produce an exothermic body that is excellent in terms of exothermic properties.

According to the third aspect of the invention, it is possible to efficiently produce an iron powder for an exothermic composition, that is excellent in terms of exothermic properties and handleability.

The invention claimed is:

1. An exothermic composition, comprising:
an iron powder with a bulk density of 0.3 to 1.5 g/cm³,
a carbon material,
a halide salt, and
water,
wherein a pore volume as measured using a mercury intrusion method of said iron powder in a range of 1 μm or more is 0.3 cm³/g or more.

2. The exothermic composition according to claim 1, wherein an average particle size of the iron powder is from 20 to 150 μm.

3. The exothermic composition according to claim 1, wherein a metal iron content in the iron powder is from 60 to 95% by mass.

4. The exothermic composition according to claim 1, wherein a BET specific surface area of the iron powder is 0.1 m$^2$/g or more.

5. The exothermic composition according to claim 1, wherein a surface layer of the iron powder is constituted by a fibrous matters that are arranged at random in three dimensions.

6. An exothermic body comprising the exothermic composition according to claim 2.

7. The exothermic composition according to claim 1, wherein a pore volume as measured using a mercury intrusion method of said iron powder in a range of 1 μm or more is 0.5 cm$^3$/g or more.

8. The exothermic composition according to claim 1, wherein a pore volume as measured using a mercury intrusion method of said iron powder in a range of 1 μm or more is 4.0 cm$^3$/g or less.

9. The exothermic composition according to claim 1, wherein a pore volume as measured using a mercury intrusion method of said iron powder in a range of 1 μm or more is 3.0 cm$^3$/g or less.

10. The exothermic composition according to claim 1, wherein an average particle size of the iron powder is from 30 μm to 150 μm.

11. The exothermic composition according to claim 1, wherein an average particle size of the iron powder is from 40 μm to 150 μm.

12. The exothermic composition according to claim 1, wherein an average particle size of the iron powder is from 30 μm to 100 μm.

13. The exothermic composition according to claim 1, wherein an average particle size of the iron powder is from 40 μm to 100 μm.

14. The exothermic composition according to claim 1, wherein a metal iron content in the iron powder is from 70% to 90% by mass.

15. The exothermic composition according to claim 1, wherein a BET specific surface area of the iron powder is 0.2 m$^2$/g or more.

16. The exothermic composition according to claim 1, wherein a BET' specific surface area of the iron powder is 50 m$^2$/g or less.

17. The exothermic composition according to claim 1, wherein a BET specific surface area of the iron powder is 40 m$^2$/g or less.

18. The exothermic composition according to claim 1, wherein said carbon material is one or more materials selected from the group consisting of activated carbon, carbon black, acetylene black, black lead, graphite, coal, and coal char.

19. The exothermic composition according to claim 1, wherein said halide salt is one or more salts selected from the group consisting of sodium chloride, potassium chloride, calcium chloride, magnesium chloride, ferrous chloride, and ferric chloride.

20. The exothermic composition according to claim 1, wherein said carbon material is present in an amount of 3 parts by mass to 30 parts by mass based on 100 parts by mass of said iron powder,
    said halide salt is present in an amount of 3 parts by mass to 30 parts by mass based on 100 parts by mass of said iron powder, and
    said water is present in an amount of 30% by mass to 70% by mass based on the total mass of said exothermic composition.

* * * * *